United States Patent
Jarrold et al.

(10) Patent No.: US 10,585,103 B2
(45) Date of Patent: Mar. 10, 2020

(54) METHODS AND COMPOSITIONS FOR RESOLVING COMPONENTS OF A VIRUS PREPARATION

(71) Applicants: INDIANA UNIVERSITY RESEARCH AND TECHNOLOGY CORPORATION, Indianapolis, IN (US); THE UNIVERSITY OF NORTH CAROLINA AT CHAPEL HILL, Chapel Hill, NC (US)

(72) Inventors: Martin F. Jarrold, Bloomington, IN (US); Aravind Asokan, Chapel Hill, NC (US); Elizabeth Pierson, Cranford, NJ (US); David Keifer, Ocean Pines, MD (US)

(73) Assignees: The Trustees of Indiana University, Bloomington, IN (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/095,985

(22) PCT Filed: Apr. 28, 2017

(86) PCT No.: PCT/US2017/030163
§ 371 (c)(1),
(2) Date: Oct. 24, 2018

(87) PCT Pub. No.: WO2017/190031
PCT Pub. Date: Nov. 2, 2017

(65) Prior Publication Data
US 2019/0086423 A1   Mar. 21, 2019

Related U.S. Application Data

(60) Provisional application No. 62/328,997, filed on Apr. 28, 2016.

(51) Int. Cl.
*G01N 33/68* (2006.01)
*H01J 49/26* (2006.01)
*C12Q 1/70* (2006.01)

(52) U.S. Cl.
CPC ........... *G01N 33/6848* (2013.01); *C12Q 1/70* (2013.01)

(58) Field of Classification Search
CPC ...... H01J 49/00; H01J 49/26; G01N 33/6848; C12Q 1/70
(Continued)

(56) References Cited

U.S. PATENT DOCUMENTS 3,019,168 A   1/1962   Taylor
5,478,745 A   12/1995  Samulski
(Continued)

FOREIGN PATENT DOCUMENTS

WO   98/11244     3/1998
WO   99/61601 A   12/1999
(Continued)

OTHER PUBLICATIONS

Analytical Ultracentrifugation as an Approach to Characterize Recombinant Adeno-Associated Viral Vectors; Brenda Burnham et al.; Human Gene Therapy Methods, vol. 26, No. 6; pp. 228-242 DOI: 10.1089/hgtb.2015.048. Epub Oct. 15, 2015.
(Continued)

*Primary Examiner* — Nicole M Ippolito
(74) *Attorney, Agent, or Firm* — Barnes & Thornburg LLP

(57) ABSTRACT

The present invention provides a method of identifying components present in a preparation of virus particles, comprising: a) analyzing the preparation of virus particles with single molecule mass spectrometry to obtain a mass
(Continued)

histogram; and b) interpreting the mass histogram of (a) to identify different components present in the preparation.

20 Claims, 7 Drawing Sheets

(58) Field of Classification Search
USPC .......................................... 250/282, 283, 288
See application file for complete search history.

(56) References Cited

U.S. PATENT DOCUMENTS

| | | | |
|---|---|---|---|
| 5,863,541 | A | 1/1999 | Samulski et al. |
| 5,869,248 | A | 2/1999 | Yuan et al. |
| 5,877,022 | A | 3/1999 | Stinchcomb et al. |
| 5,882,652 | A | 3/1999 | Valdes et al. |
| 5,905,040 | A | 5/1999 | Mazzara et al. |
| 5,916,563 | A | 6/1999 | Young et al. |
| 6,013,487 | A | 1/2000 | Mitchell |
| 6,083,702 | A | 7/2000 | Mitchell et al. |
| 6,156,303 | A | 12/2000 | Russell et al. |
| 6,183,950 | B1* | 2/2001 | Madonna ................. H01J 49/04 435/5 |
| 7,314,912 | B1 | 1/2008 | Hallek et al. |
| 8,409,870 | B2* | 4/2013 | Van Wuijckhuijse ...................... H01J 49/0418 436/173 |
| 9,095,793 | B2* | 8/2015 | Flagan ....................... B03C 1/30 |
| 2007/0254352 | A1 | 11/2007 | Schaffer et al. |
| 2010/0227310 | A1 | 9/2010 | Manalis et al. |
| 2010/0234837 | A1* | 9/2010 | Alfano .................... G06N 10/00 606/16 |
| 2013/0124099 | A1 | 5/2013 | Ecker et al. |
| 2014/0346344 | A1* | 11/2014 | Chen .................. G01N 33/4833 250/283 |

FOREIGN PATENT DOCUMENTS

| | | |
|---|---|---|
| WO | 00/28004 A | 5/2000 |
| WO | 00/28061 A | 5/2000 |
| WO | 01/92551 A2 | 5/2001 |

OTHER PUBLICATIONS

Chimeric Parvovirus B19 Capsids for the Presentation of Foreign Epitopes; Caroline S. Brown et al.; Virology 198, pp. 477-488 (1994).
Parvoviridae: The Viruses and Their Replication; Bernard N. Fields et al.; Virology, vol. 2, Chapter 69, pp. 2327-2359; (4th ed., Lippincott-Raven Publishers).
Hepatitis E Virus; Suzanne U. Emerson et al.; Virology, vol. 2, Chapter 70; (4th ed., Lippincott-Raven Publishers).
Human Adeno-Associated Virus Type 5 Is Only Distantly Related to Other Known Primate Helper-Dependent Parvoviruses; Ursula Bantel-Schall et al.; Journal of Virology, vol. 73, pp. 939-947 (Feb. 1999).
Several Log Increase in Therapeutic Transgene Delivery by Distinct Adeno-Associated Viral Serotype Vectors; Hengjun Chao et al.; Molecular Therapy vol. 2, No. 6, pp. 619-623 (Dec. 2000).
Cloning of Adeno-Associated Virus Type 4 (AAV4) and Generation of Recombinant AAV4 Particles; John A. Chiorini et al.; Journal of Virology, vol. 71, pp. 6823-6833 (Sep. 1997).
Cloning and Characterization of Adeno-Associated Virus Type 5; John A. Chiorini et al.; Journal of Virology, vol. 73, pp. 1309-1319 (Feb. 1999).
Clades of Adeno-Associated Viruses Are Widely Disseminated in Human Tissues; Guangping Gao et al.; Journal of Virology, vol. 78, pp. 6381-6388 (Jun. 2004).
Novel Adeno-Associated Viruses from Rhesus Monkeys as Vectors for Human GeneTherapy; Guang-Ping Gao et al.; National Academy of Sciences, vol. 99, No. 18, pp. 11854-11859 (Sep. 3, 2002).
Stable Alteration of Pre-mRNA Splicing Patterns by Modified U7 Small Nuclear RNAs; Linda Gorman et al.; National Academy of Sciences, vol. 95, No. 9, pp. 4929-4934 (Apr. 28, 1998).
Incorporation of Tumor-Targeting Peptides into Recombinant Adeno-associated Virus Capsids; Mirta Grifman et al.; Molecular Therapy, vol. 3, No. 6, pp. 964-975 (Jun. 2001).
Characterization of Tissue Tropism Determinants of Adeno-Associated Virus Type 1; Bernd Hauck et al.; Journal of Virology, vol. 77, No. 4, pp. 2768-2774 (Feb. 2003).
Single-Molecule Mass Spectrometry, David Z. Keifer et al.; Mass Spectrometry Reviews, vol. 36 pp. 715-733 (2017).
Charge Detection Mass Spectrometry with Almost Perfect Charge Accuracy; David Z. Keifer et al.; Analytical Chemistry, vol. 87, pp. 10330-10337 (2015).
Two novel adeno-associated viruses from cynomolgus monkey: pseudotyping characterization of capsid protein; Seiichiro Mori et al.; Virology 330, pp. 375-383 (2004).
Nucleotide Sequencing and Generation of an Infectious Clone of Adeno-Associated Virus 3; Shin-ichi Muramatsu et al.; Virology vol. 221; Article No. 0367; pp. 208-217 (1996).
Parvovirus Particles as Platforms for Protein Presentation; Koichi Miyamura et al.; National Academy of Sciences, vol. 91, No. 18, pp. 8507-8511 (Aug. 30, 1994).
Use of Adeno-Associated Virus as a General Transduction Vector for Mammalian Cells; N. Muzyczka; Current Topics in Microbiology and Immunology, vol. 158, pp. 97-129 (1992).
Structure of Adeno-Associated Virus Type 4, Eric Padron et al.; Journal of Virology, vol. 79, No. 8, pp. 5047-5058 (Apr. 2005).
Charge Detection Mass Spectrometry for Single Ions with an Uncertainty in the Charge Measurement of 0.65 e; Elizabeth E. Pierson et al.; Journal American Society for Mass Spectrometry, vol. 26, pp. 1213-1220 (2015).
Spliceosome-mediated RNA trans-splicing as a tool for gene therapy; M. Puttaraju et al.; Nature Biotechnology, vol. 17, pp. 246-252 (Mar. 1999).
Nucleotide Sequence and Genome Organization of Human Parvovirus B19 Isolated from the Serum of a Child during Aplastic Crisis; Rosemary O. Shade et al.; Journal of Virology, vol. 58, No. 3, pp. 921-936 (Jun. 1986).
RNA Interference; Phillip A. Sharp et al.; American Association for the Advancement of Science; Science, New Series, vol. 287, No. 5462, pp. 2431-2433 (Mar. 31, 2000).
Insertional Mutagenesis at Positions 520 and 584 of Adeno-Associated Virus Type 2 (AAV2) Capsid Gene and Generation of AAV2 Vectors with Eliminated Heparin-Binding Ability and Introduced Novel Tropism; Ziangqun Shi, et al.; Human Gene Therapy, vol. 17, pp. 353-361 (Mar. 2006).
Nucleotide Sequence and Organization of the Adeno-Associated Virus 2 Genome; Arun Srivastava et al.; Journal of Virology, vol. 45, No. 2, pp. 555-564 (Feb. 1983).
The Three-Dimensional Structure of Canine Parvovirus and Its Functional Implications; Jun Tsao et al.; American Association for the Advancement of Science, Science, New Series, vol. 251, No. 5000, pp. 1456-1464 (Mar. 22, 1991).
Structure of Adeno-Associated Virus Serotype 5; Robert W. Walters et al.; Journal of Virology, vol. 78, No. 7, pp. 3361-3371 (Apr. 2004).
Expanding the Genetic Code; Lei Wang et al.; Annual Review of Biophysics and Biomolecular Structure, vol. 35, pp. 225-249 (2006).
Canine Parvovirus Capsid Structure, Analyzed at 2.9 Å Resolution; Qing Xie et al.; Journal of Molecular Biology, vol. 264, pp. 497-520 (1996).
The atomic structure of adeno-associated virus (AAV-2), a vector for human gene therapy; Qing Xie et al.; PNAS, vol. 99, No. 16, pp. 10405-10410 (Aug. 6, 2002).
Gene Therapy Vectors Based on Adeno-Associated Virus Type 1; Weidong Xiao et al.; Journal of Virology, vol. 73, No. 5, pp. 3994-4003 (May 1999).
Protein transport: The nonclassical ins and outs; Ann E. Cleves; Current Biology, vol. 7, No. 5, pp. 318-320 (1997).

(56) References Cited

OTHER PUBLICATIONS

Detection of Late Intermediates in Virus Capsid Assembly by Charge Detection Mass Spectrometry; Elizabeth E. Pierson et al.; Journal of the American Chemical Society, vol. 136, pp_ 3536-3541 (2014).
Bioconjugate Techniques; Hermanson;Academic Press, 1st Edition (1996).
PCT International Search Report and Written Opinion completed by the ISA/US on Jun. 19, 2017 and issued in connection with PCT/US2017/030163.
Pierson, et al. "Charge Detection Mass Spectrometry Identifies Preferred Non-Icosahedral Polymorphs in the Self-Assembly of Woodchuck Hepatitis Virius Capsids." Journal of Molecular Biology, vol. 428, Issue 2, pp. 292-300, Jan. 29, 2016.
Kiefer et al., "Charge detection mass spectrometry of bacteriophage P22 procapsid distributions above 20 MDa", Rapid Commun. Mass Spectrom 2014, 28, 483-488.
Uetrecht et al., "Stability and Shape of Hepatitis B Virus Capsids In Vacuo", Angew. Chem. Int. Ed. 2008, 47, 6247-6251.
Uetrecht et al., "High-resolution mass spectrometry of viral assemblies: Molecular composition and stability of dimorphic hepatitis B virus capsids", PNAS 2008, vol. 105, 9216-9920.
Fuerstenau et al., "Mass Spectrometry of an Intact Virus", Agnew. Chem. 2001, 559-562.
Supplemental European Search Report for European Patent Application No. 17790559.3 dated Nov. 12, 2019 (11 pages).
Pierson et al., "Detection of 1-15 Late Intermediates in Virus Capsid Assembly by Charge Detection Mass Spectrometry", Journal of the American Chemical Society, vol. 136, No. 9, Feb. 19, 2014, 3536-3541.

\* cited by examiner

METHODS AND COMPOSITIONS FOR RESOLVING COMPONENTS OF A VIRUS PREPARATION

CROSS-REFERENCE TO RELATED APPLICATIONS

This application is a national stage entry under 35 U.S.C. § 371 of PCT International Application No. PCT/US2017/030163, filed Apr. 28, 2017, and claims the benefit under 35 U.S.C. § 119(e) of U.S. Provisional Patent Application No. 62/328,997, filed Apr. 28, 2016, the disclosures of which are expressly incorporated by reference in their entireties.

GOVERNMENT SUPPORT CLAUSE

This invention was made with government support under HL089221 and HL112761 awarded by the National Institutes of Health and CHE1531823 and CHE0832651 awarded by the National Science Foundation. The Government has certain rights in the invention.

FIELD OF THE INVENTION

The present invention relates to methods and compositions for resolving components of a virus preparation with mass spectrometry.

BACKGROUND OF THE INVENTION

Mass spectrometry (MS) has been the driving force behind the development of proteomics and has had a large impact in the fields of molecular and cellular biology. Concurrently, there has been growing interest in using native mass spectrometry to investigate protein complexes and other assemblies with masses into the MDa range. However, there are challenges associated with the mass analysis of such large objects. The main issue is that the peaks in the m/z spectrum broaden and shift due to mass heterogeneity, either intrinsic or due to complex formation. Poorly resolved peaks in the m/z spectrum prevent charge state assignment and subsequent mass deduction. In particular, viruses have a proclivity for being heterogeneous in mass because they have the ability to encapsidate varying amounts of genetic material. Earlier studies demonstrated the feasibility of using time-of-flight mass spectrometry to measure the m/z spectrum of the ~2.5 MDa bacteriophage MS2 capsid, albeit without sufficient charge state resolution to calculate an accurate mass of the complex. More recently, high resolution m/z spectra of empty hepatitis B virus (HBV) capsids assembled from truncated proteins lacking the C-terminal RNA-binding domain have been reported. However, the m/z spectrum for HBV assembled from the full-length capsid protein lacked charge state resolution due to heterogeneity.

AAV vectors have emerged at the forefront of gene therapy due to their lack of pathogenicity, relatively low immunogenicity and persistent gene expression in different tissue types. From a structural perspective, this helper-dependent parvovirus has a non-enveloped, icosahedral capsid ~25 nm in diameter that packages a single-stranded DNA (ssDNA) genome ~4.7 kb in length. Despite promising outcomes in several clinical trials, a recurring concern noted in hemophilia gene therapy clinical trials is the potential for vector dose-related immunotoxicity in patients. Although resolvable by administration of anti-inflammatory steroids such as methyl prednisolone, several studies have indicated that the composition of clinical AAV vector preparations can influence these outcomes. In this regard, recombinant AAV vector preparations can contain different levels of full or partial genome-containing particles as well as empty virions. Such particle diversity can be attributed to multiple factors such as genome packaging efficiency, production methods, downstream purification techniques and storage conditions.

Though AAV packages ssDNA, the use of a self-complementary (sc) DNA genome bypasses the rate-limiting second-strand synthesis process and leads to more efficient and rapid onset of trans gene expression. scDNA is a double-stranded DNA molecule formed by intramolecular base paring of two single-stranded vectors joined by a hairpin. Because scDNA is packaged as a single strand, the total length of the DNA is limited to approximately 4.7 kb so that the effective length of the unique transgene sequence is halved. Upon release into the host cell, scDNA anneals into the base-paired form. Though scAAV vectors show promise in the clinic, their characterization remains a challenge.

Currently, electron microcopy (EM) is utilized to characterize the ultrastructural composition of AAV vector preparations. Although useful, this method is time consuming, subjective, and relies on large datasets to obtain an accurate representation of AAV particle diversity. While this technique can distinguish empty virions from genome-containing particles, EM may not help resolve partial or truncated genome-containing particles and free vector genomic DNA. Also, current quantitative PCR-based methods, cannot help distinguish between partial/truncated vector genomes from fully packaged genomes. Recently, Burnham et al demonstrated the use of analytical ultracentrifugation as a low-resolution technique for the characterization of recombinant AAV vectors. Thus, the development of cutting edge methods that can help analyze ultrastructural heterogeneity in recombinant AAV vector preparations at high resolution is an unmet need in the gene therapy field.

The present invention addresses a need in the art for protocols that allow for resolution of different components of a preparation of virus particles.

SUMMARY OF THE INVENTION

In one embodiment, the present invention provides a method of identifying components present in a preparation of virus particles, comprising: a) subjecting the preparation of virus particles to mass spectrometry, such as single molecule mass spectrometry, to separate components of the preparation of virus particles; and b) identifying the separated components of the preparation of virus particles. This method can further comprise the step of producing a mass histogram of the separate components of the preparation of virus particles and identifying the separated components of the preparation of virus particles based on the mass histogram.

In particular embodiments of the invention, the single molecule mass spectrometry can be carried out or performed by time of flight mass spectrometry, charge detection mass spectrometry, quadrupole ion trap mass spectrometry, Fourier transform ion cyclotron resonance and/or Orbitrap mass spectrometry. In some embodiments the single molecule mass spectrometry can be carried out or performed with a micromechanical/nanomechanical oscillator. These approaches for carrying out single molecule mass spectrometry can be employed individually or in any combination.

In some embodiments, the single molecule mass spectrometry can be carried out or performed on a commercial mass spectrometer retro-fitted for single molecule measurements.

Several embodiments of the invention are described by the following enumerated clauses:

1. A method of identifying components present in a preparation of virus particles, the method comprising:
   a) subjecting the preparation of virus particles to mass spectrometry to produce an ion;
   b) measuring the charge of the ion;
   c) measuring the mass-to-charge ratio of the ion; and
   d) identifying the components based on the mass of the ion.
2. The method of clause 1, wherein mass spectrometry comprises single molecule mass spectrometry.
3. The method of clause 1 or 2, wherein mass spectrometry comprises charge detection mass spectrometry.
4. The method of any preceding clause, comprising trapping the ion for at least 50 ms.
5. The method of any preceding clause, wherein measuring the charge of the ion comprises measuring oscillation frequency.
6. The method of any preceding clause, wherein measuring the mass-to-charge ratio of the ion comprises measuring trapping time.
7. The method of any preceding clause, wherein the components comprise a single-stranded genome or a self-complementary genome.
8. The method of any preceding clause, wherein the virus particles comprise an impurity.
9. The method of any preceding clause, wherein the components comprise one or more of full genome-containing virus particles, partial genome-containing virus particles, and genome-free virus particles.
10. The method of any preceding clause, wherein the method does not comprise electron microscopy.
11. The method of any preceding clause, further comprising heating the virus particles to monitor disassembly.
12. The method of clause 11, wherein the virus particles are heated to at least 35° C.
13. The method of clause 11 or 12, wherein the virus particles are heated to at least 50° C.
14. The method of any preceding clause, further comprising producing a mass histogram of the components and identifying separated components based on the mass histogram.
15. The method of any preceding clause, wherein the virus particles are selected from the group consisting of adeno-associated virus (AAV), adenovirus, lentivirus, retrovirus, herpesvirus, poxvirus, paramyxovirus, baculovirus, reovirus, alphavirus, flavivirus, and combinations thereof.
16. The method of any preceding clause, wherein one or more of the virus particles are complexed with an exogenous entity.
17. The method of clause 16, wherein the exogenous entity is selected from the group consisting of a protein, a nucleic acid, a carbohydrate molecule, and combinations thereof.
18. The method of any preceding clause, wherein the method is carried out in about 20 minutes.
19. A method of identifying components present in a preparation of virus particles, the method comprising:
   a) subjecting the preparation of virus particles to mass spectrometry and
   b) identifying the components of the preparation of the virus particles.
20. The method of clause 19, wherein mass spectrometry comprises charge detection mass spectrometry.
21. The method of clause 19 or 20, further comprising distinguishing the components based on differences in masses of ions resulting from the components.
22. The method of any of clauses 19 to 21, wherein the virus particles comprise an impurity.
23. The method of clause 22, further comprising detecting the impurity based on differences in masses of ions resulting from the components.
24. The method of any of clauses 19 to 23, wherein the components comprise one or more of full genome-containing virus particles, partial genome-containing virus particles, and genome-free virus particles.
25. The method of any of clauses 19 to 24, wherein the method does not comprise electron microscopy.
26. The method of any of clauses 19 to 25, further comprising heating the virus particles to monitor disassembly.
27. The method of clause 27, wherein the virus particles are heated to at least 35° C.
28. The method of clause 26 or 27, wherein the virus particles are heated to at least 50° C.
29. The method of any of clauses 19 to 28, further comprising producing a mass histogram of the components and identifying separated components based on the mass histogram.
30. The method of any of clauses 19 to 29, wherein the virus particles are selected from the group consisting of adeno-associated virus (AAV), adenovirus, lentivirus, retrovirus, herpesvirus, poxvirus, paramyxovirus, baculovirus, reovirus, alphavirus, flavivirus, and combinations thereof.
31. The method of any of clauses 19 to 30, wherein one or more of the virus particles are complexed with an exogenous entity.
32. The method of clause 31, wherein the exogenous entity is selected from the group consisting of a protein, a nucleic acid, a carbohydrate molecule, and combinations thereof.
33. The method of any of clauses 19 to 32, wherein the method is carried out in about 20 minutes.
34. A method of identifying components present in a preparation of virus particles, comprising:
   a) subjecting the preparation of virus particles to single molecule mass spectrometry to separate components of the preparation of virus particles; and
   b) identifying the separated components of the preparation of virus particles.
35. The method of clause 34, further comprising the step of producing a mass histogram of the separate components of the preparation of virus particles and identifying the separated components of the preparation of virus particles based on the mass histogram.
36. The method of clause 34 or 35, wherein the components of the preparation of virus particles are selected from the group consisting of full genome-containing virus particles, partial genome-containing virus particles, genome-free virus particles, empty virus capsids and fragments thereof, genomic components and fragments thereof, packaged genomes and fragments thereof, unpackaged nucleic acid, contaminants, and any combination thereof.
37. The method of any of clauses 34 to 36, wherein the single molecule mass spectrometry is performed by time of flight mass spectrometry, charge detection mass spectrometry, quadrupole ion trap mass spectrometry, Fourier transform ion cyclotron resonance, Orbitrap mass spectrometry or carried out using a micromechanical/nanomechanical oscillator.

38. The method of any of clauses 34 to 37, wherein the single molecule mass spectrometry is carried out on a commercial mass spectrometer retro-fitted for single molecule measurements.
39. The method of any of clauses 34 to 38, wherein the virus is selected from the group consisting of an adeno-associated virus (AAV), an adenovirus, a lentivirus, a retrovirus, a herpesvirus, a poxvirus (vaccinia, myxoma), a paramyxovirus (measles, RSV, Newcastle disease virus), a baculovirus, a reovirus, an alphavirus, a flavivirus, and any combination thereof.
40. The method of any of clauses 34 to 39, further comprising identifying virus particles complexed with an exogenous entity.
41. The method of clause 40, wherein the exogenous entity is a protein, a nucleic acid and/or a carbohydrate molecule.
42. The method of any of clauses 34 to 41, wherein the preparation is a research grade preparation.
43. The method of any of clauses 34 to 41, wherein the preparation is a GMP grade preparation.
44. The method of any of clauses 34 to 41, wherein the preparation is a commercial preparation.
45. The method of any of clauses 34 to 44, wherein the method is carried out in about 20 minutes.

These and other aspects of the invention are addressed in more detail in the description of the invention set forth below.

BRIEF DESCRIPTION OF THE DRAWINGS

FIG. 4a is a mass histogram for AAV8 packaging a scGFP genome.

FIG. 4b is a TEM image of the sample of FIG. 4a.

FIG. 5a is a scatter plot showing charge versus mass for AAV8 packaging a scGFP genome, where the diagonal lines are lines of constant m/z FIG. 5b is a m/z histogram for the AAV8 packaging a scGFP genome of FIG. 5a.

DETAILED DESCRIPTION

Figure 1:
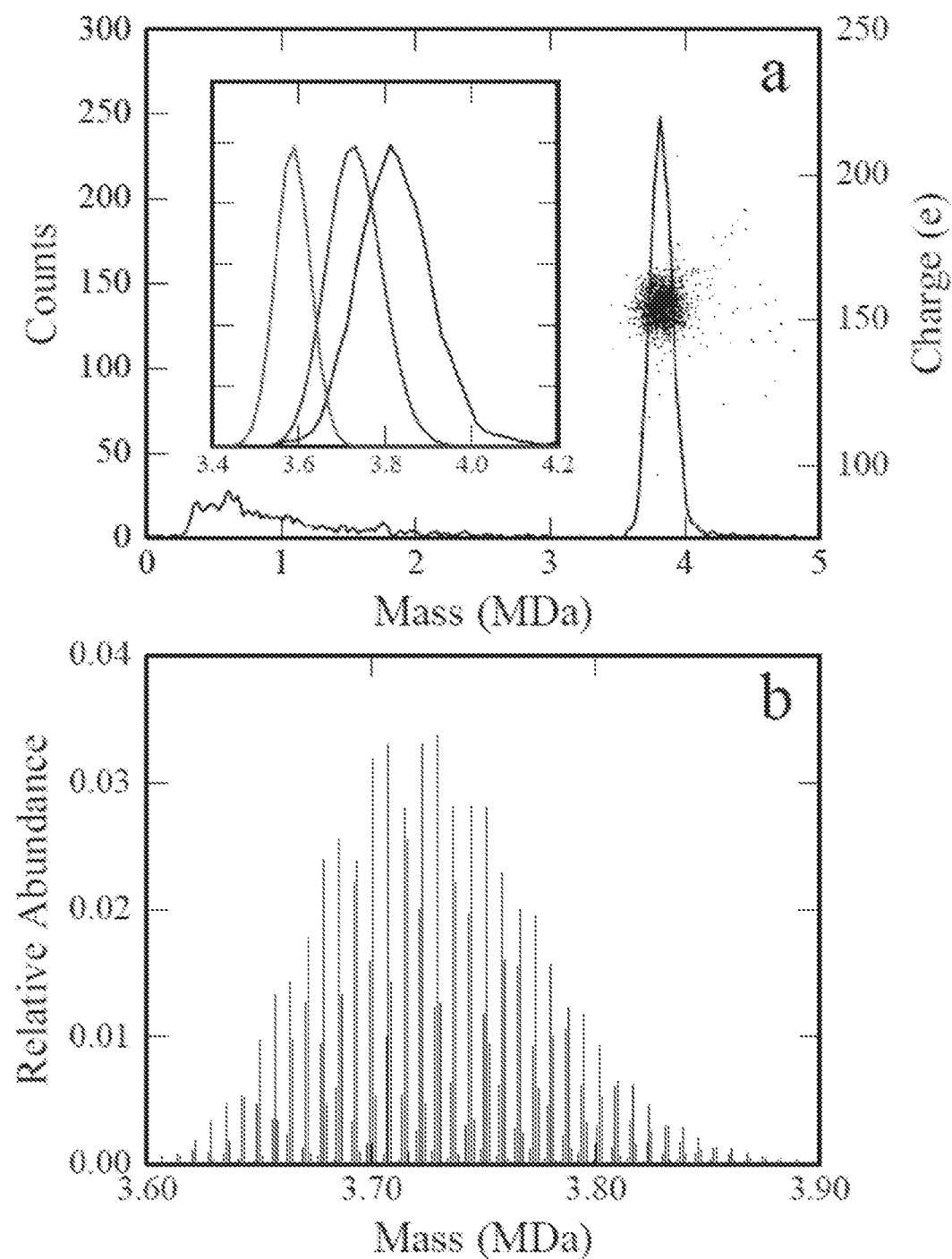
FIG. 1a is a CDMS mass histogram measured for empty capsids separated from AAV8 vectors packaging a CBA-Luc genome.
FIG. 1b is a mass distribution showing the masses and abundances of all possible VP1, VP2 and VP3 compositions in a 1:1:10 ratio determined from a multinomial distribution.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference herein in their entirety.

The present invention provides an improved approach for resolving different components of a virus preparation. As such, the present invention provides a method of identifying components present in a preparation of virus particles (e.g., naturally occurring virus particles, non-naturally occurring virus particles, a mixture of naturally occurring and non-naturally occurring virus particles, recombinant virus particles and any combination thereof), comprising: a) subjecting the preparation of virus particles to mass spectrometry; and b) identifying the separated components of the preparation of virus particles. In some embodiments, the mass spectrometry is single molecule mass spectrometry. Mass spectrometry may separate components of the preparation of virus particles. This method can further comprise the step of producing a mass histogram of the separate components of the preparation of virus particles and identifying the separated components of the preparation of virus particles based on the mass histogram.

In another embodiment, the present invention provides a method of resolving components present in a preparation of virus particles (e.g., naturally occurring virus particles, non-naturally occurring virus particles, a mixture of naturally occurring and nonnaturally occurring virus particles, recombinant virus particles and any combination thereof), wherein components of the preparation of virus particles have been or are being separated, comprising: a) analyzing the preparation of virus particles with mass spectrometry, such as single molecule mass spectrometry, to obtain a mass histogram; and b) interpreting the mass histogram of (a) to differentiate components of the preparation of virus particles.

In some embodiments of this invention, the components of the preparation of virus particles can be one or more of the following: full genome-containing virus particles, partial genome-containing virus particles, genome-free virus particles, empty virus capsids and fragments thereof, genomic components and fragments thereof, packaged genomes and fragments thereof, unpackaged nucleic acid, contaminants, and any combination thereof.

In embodiments in which the virus under analysis is an enveloped virus, the methods of this invention can also be used to differentiate membrane components, membrane fragments, membranes and/or membrane fragments complexed with an exogenous entity, such a protein, nucleic acid and/or carbohydrate entity.

Thus, the present invention is directed to analyzing the preparation of virus particles by any method where the masses of individual ions are determined to overcome sample heterogeneity and obtain a mass histogram of the constituents. Nonlimiting examples of single molecule mass spectrometry approaches that can be employed in the methods of this invention include time of flight mass spectrometry with a cryogenic detector, charge detection mass spectrometry (CDMS), quadrupole ion trap mass spectrometry with optical detection and charge detection, Fourier transform ion cyclotron resonance, Orbitrap mass spectrometry and micromechanical/nanomechanical oscillators. A detailed description of various single molecule mass spectrometry approaches included in this invention can be found in Keifer & Jarrold ("Single molecule mass spectrometry" *Mass Spectrometry Reviews*; DOI 10.1002/mas.21495 (2016) Wiley Periodicals, Inc.; the entire contents of which are incorporated by reference herein).

Charge detection mass spectrometry (CDMS) is a single particle technique, where the m/z and z of individual ions are measured concurrently, thereby allowing direct determination of the mass of each ion. Examples of CDMS are described in Keifer et al. (*Anal. Chem.*, 2015, 87 (20), pp 10330-10337) and Pierson et al. (*J. Am. Soc. Mass Spectrom.* (2015) 26:1213-1220); the entire contents of which are incorporated by reference herein. The methods described herein include using CDMS to analyze heterogeneous mixtures other large assemblies that are intractable by conventional MS methods. In some embodiments, CDMS may be used to determine masses of ions beyond about 1 MDa, about 10 MDa, about 25 MDa, about 50 MDa, or 100 MDa and/or to analyze mixtures of heavy ions. In some embodiments, CDMS may be used to determine masses of ions of about 1 MDa to about 100 GDa, about 10 MDa to about 100 GDa, about 25 MDa to about 100 GDa, about 50 MDa to about 100 GDa, about 100 MDa to about 100 GDa, about 1 MDa to about 10 GDa, about 10 MDa to about 10 GDa, about 25 MDa to about 10 GDa, about 50 MDa to about 10 GDa, about 100 MDa to about 10 GDa, about 1 MDa to about 1 GDa, about 10 MDa to about 1 GDa, about 25 MDa to about 1 GDa, about 50 MDa to about 1 GDa, or about 100 MDa to about 1 GDa. The methods discussed herein may improve the mass resolution.

In some embodiments, the mass spectrometry methods described herein further comprise utilizing a reduced pressure to extend trapping time. The trapping time may be greater than about 10 ms, about 25 ms, about 50 ms, about 75 ms, about 100 ms, about 150 ms, about 200 ms, or about 300 ms. Additionally, the trapping time may be from about 10 ms to about 1000 ms, about 25 ms to about 1000 ms, about 50 ms to about 1000 ms, about 75 ms to about 1000 ms, about 100 ms to about 1000 ms, about 150 ms to about 1000 ms, about 200 ms to about 1000 ms, or about 300 ms to about 1000 ms.

In particular embodiments of the invention, the single molecule mass spectrometry can be carried out or performed by time of flight mass spectrometry, charge detection mass spectrometry, quadrupole ion trap mass spectrometry, Fourier transform ion cyclotron resonance and/or Orbitrap mass spectrometry. In some embodiments the single molecule mass spectrometry can be carried out or performed with a micromechanical/nanomechanical oscillator. These approaches for carrying out single molecule mass spectrometry can be employed individually or in any combination.

Sample preparation for carrying out the methods of this invention is carried out according to protocols described herein as well as protocols known in the art for single molecule mass spectrometry methods. Such methods can involve transferring a sample to a solution containing a volatile salt. In some embodiments, the salt can be ammonium acetate, although other salts may be used in certain embodiments.

In some embodiments, the single molecule mass spectrometry can be carried out or performed on a commercial mass spectrometer retro-fitted for single molecule measurements. As one nonlimiting example, a single molecule detector can be retrofitted to an existing instrument (e.g., a commercial instrument) that would allow single molecule mass measurements to be performed. A nonlimiting example of a commercial instrument is a quadrupole time-of-flight (QTOF) mass spectrometer and the single molecule detector could be added after the TOF analyzer.

A virus of this invention can be any virus that can be part of a preparation (e.g., a virus preparation or vector preparation), which can be a research grade preparation (e.g., for preclinical evaluation), a good manufacturing practice (GMP) preparation (e.g., a clinical preparation for clinical evaluation) and/or a commercial preparation (e.g. a commercially available therapeutic product). These virus or vector preparations can be obtained from different production methods involving bacterial, yeast, insect, avian, reptilian and/or mammalian cell culture systems and/or involving transfection/electroporation-based, baculoviral, helper virus-based, lentiviral, retroviral and/or producer cell systems.

A virus of this invention includes but is not limited to an adeno-associated virus (AAV), an adenovirus, a lentivirus, a retrovirus, a herpesvirus, a poxvirus (vaccinia, myxoma), a paramyxovirus (measles, RSV, Newcastle disease virus), a baculovirus, a reovirus, an orthomyxovirus, an alphavirus, a flavivirus, and any combination thereof, as well as any other virus now known or later identified.

In some embodiments of this invention, the preparation of viruses can comprise virus particles complexed with an exogenous entity. Accordingly the methods of this invention can be used to resolve and/or identify virus particles complexed with an exogenous entity. Nonlimiting examples of an exogenous entity include a protein, nucleic acid, carbohydrate molecule and any combination thereof.

The methods of the present invention provide an improvement in the art of resolving components of a virus preparation and/or determining the purity and/or homogeneity of a virus preparation. As one example, it is known that recombinant adeno-associated virus (AAV) vectors are promising vectors for human gene therapy. A recurring concern noted in preclinical and clinical studies is the potential for vector dose-related toxicity as indicated by detection of liver transaminases in serum. Although this toxicity is resolvable by administration of anti-inflammatory steroids such as methyl prednisone, permanent loss of gene expression has been noted in some cases. Notably, these studies suggest that the composition of clinical AAV vector preparations can influence these outcomes. The development of cutting edge methods that can help analyze ultrastructural heterogeneity of AAV vector preparations at high resolution is currently an unmet need in the gene therapy field.

The present invention provides a new method based on single molecule mass spectrometry (e.g., charge detection mass spectrometry (CDMS)) that can resolve the entire mass landscape of whole virus particles, capsid intermediates and viral genomes. Specifically, mapping can be carried out of the entire mass landscape of empty genome-free, partial genome-containing, and full genome-packaging virus particles as well as contaminants such as capsid fragments and genomes from, e.g., thermally induced disassembly.

The mass spectrometry methods described herein dramatically shorten analysis time from hours to minutes in acquiring a high resolution profile of a virus composition or preparation as compared with, e.g., electron microscopy, analytical ultracentrifugation and analysis employing nucleic acid amplification protocols such as polymerase chain reaction (PCR). The methods of this invention can be seamlessly integrated into existing quality assurance/quality control (QA/QC) protocols for viral vector analysis. No other currently available methods or assays are capable of accurately identifying and/or distinguishing partially filled particles.

In some embodiments, the methods of this invention can be carried out wherein the method is carried out in about 20, 25, 30, 35, 40, 35, 50, 55, 60, 65, 70, 75, 80, 85, 90, 95 or 100 minutes. In some embodiments, the methods of this invention can be carried out in about 1, 2, 3, 4, 5, 6, 7, 8, 9, 10, 11, or 12 hours.

In some embodiments of this invention, the methods can be carried out in about 25%, 50%, 75% or 90% less time than would be required to resolve components of a virus preparation using standard protocols such as electron microscopy, analytical centrifugation and/or nucleic acid amplification (e.g., PCR). The present invention is also a substantial improvement over such standard methods for resolving components of a virus preparation. In particular, the methods of the present invention allow for distinguishing empty and genome-free virus particles from partial and/or full-genome containing virus particles. Furthermore, the methods of the present invention allow for resolving any components and/or potential contaminants in any virus preparation that range in mass from about 10 kDa to about 100 GDa.

In some embodiments, the methods of the present invention can be employed to establish the mass and stoichiometry of virus capsids complexed with or chemically conjugated to exogenous protein, nucleic acid and/or carbohydrate moieties.

In some embodiments, the methods of the present invention can be employed to establish purity and/or homogeneity of a virus preparation.

In some embodiments of this invention, the methods described herein can be employed to distinguish between virus particles produced in cells of different species (e.g., between an alphavirus produced in an animal cell and an alphavirus produced in an insect cell). The methods of this invention can also be used to resolve differences in virus particle and/or virus capsid structure, morphology, orientation, size, chemical status (e.g., methylated or non-methylated) and the like. The methods of this invention can also be employed to identify differences in lipid, protein and/or nucleic acid content among virus particles or components of a preparation of this invention.

Definitions

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L, and/or V, this language also indicates that the amino acid can be selected from any subset of these amino acid(s) for example A, G, I, or L; A, G, I, or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 25%, 35%, 50%, 75%, 80%, 85%, 90%, 95%, 97% or more.

As used herein, the terms "enhance," "enhances," "enhancement" and similar terms indicate an increase of at least about 5%, 10%, 20%, 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al. (2004) *J. Virology* 78:6381-6388; Moris et al. (2004) *Virology* 33-:375-383; and Table 1).

TABLE 1

GenBank accession numbers for AAV serotypes/isolates

| AAV Serotypes/Isolates | GenBank Accession Number |
|---|---|
| Clonal Isolates | |
| Avian AAV ATCC VR-865 | AY186198, AY629583, NC_004828 |
| Avian AAV strain DA-1 | NC_006263, AY629583 |
| Bovine AAV | NC_005889, AY388617 |

TABLE 1-continued

GenBank accession numbers for AAV serotypes/isolates

| AAV Serotypes/Isolates | GenBank Accession Number |
| --- | --- |
| AAV4 | NC_001829 |
| AAV5 | AY18065, AF085716 |
| Rh34 | AY243001 |
| Rh33 | AY243002 |
| Rh32 | AY243003 |
| Clade A | |
| AAV1 | NC_002077, AF063497 |
| AAV6 | NC_001862 |
| Hu 48 | AY530611 |
| Hu 43 | AY530606 |
| Hu 44 | AY530607 |
| Hu 46 | AY530609 |
| Clade B | |
| Hu 19 | AY530584 |
| Hu 20 | AY530586 |
| Hu 23 | AY530589 |
| Hu 22 | AY530588 |
| Hu 24 | AY530590 |
| Hu 21 | AY530587 |
| Hu 27 | AY530592 |
| Hu 28 | AY530593 |
| Hu 29 | AY530594 |
| Hu 63 | AY530624 |
| Hu 64 | AY530625 |
| Hu 13 | AY530578 |
| Hu 56 | AY530618 |
| Hu 57 | AY530619 |
| Hu 49 | AY530612 |
| Hu 58 | AY530620 |
| Hu 34 | AY530598 |
| Hu 35 | AY530599 |
| AAV2 | NC_001401 |
| Hu 45 | AY530608 |
| Hu 47 | AY530610 |
| Hu 51 | AY530613 |
| Hu 52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| AAV 3 | NC_001729 |
| AAV 3B | NC 001863 |
| Hu 9 | AY530629 |
| Hu 10 | AY530576 |
| Hu 11 | AY530577 |
| Hu 53 | AY530615 |
| Hu 55 | AY530617 |
| Hu 54 | AY530616 |
| Hu 7 | AY530628 |
| Hu 18 | AY530583 |
| Hu 15 | AY530580 |
| Hu 16 | AY530581 |
| Hu 25 | AY530591 |
| Hu 60 | AY530622 |
| Ch 5 | AY243021 |
| Hu 3 | AY530595 |
| Hu 1 | AY530575 |
| Hu 4 | AY530602 |
| Hu 2 | AY530585 |
| Hu 61 | AY530623 |
| Clade D | |
| Rh62 | AY530573 |
| Rh48 | AY530561 |
| Rh54 | AY530567 |
| Rh55 | AY530568 |

TABLE 1-continued

GenBank accession numbers for AAV serotypes/isolates

| AAV Serotypes/Isolates | GenBank Accession Number |
| --- | --- |
| Cy2 | AY243020 |
| AAV 7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| AAV9 (Hu14) | AY530579 |
| Hu31 | AY530596 |
| Hu32 | AY530597 |

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as the GenBank® Database. See, e.g., GenBank Accession Numbers NC_044927, NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al. (1983) *J. Virology* 45:555; Chiarini et al. (1998) *J. Virology* 71:6823; Chiarini et al. (1999) *J. Virology* 73:1309; Bantel-Schaal et al. (1999) *J. Virology* 73:939; Xiao et al. (1999) *J. Virology* 73:3994; Muramatsu et al. (1996) *Virology* 221:208; Shade et al. (1986) *J.*

*Virology.* 58:921; Gao et al. (2002) *Proc. Nat. Acad. Sci. USA* 99:11854; Moris et al. (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al. (2002) *Proc. Nat. Acad. Sci.* 99:10405-10), AAV4 (Padron et al. (2005) *J. Virology* 79:5047-58), AAV5 (Walters et al. (2004) *J Virology* 78: 3361-71) and CPV (Xie et al. (1996) *J. Mol. Biol.* 6:497-520 and Tsao et al. (1991) *Science* 251:1456-64).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

As used herein, by "isolate: or "purify" (or grammatical equivalents) a virus vector, it is meant that the virus vector is at least partially separated from at least some of the other components in the starting material. In representative embodiments an "isolated" or "purified virus vector is enriched by at least about 10-fold, 100-fold, 1000-fold, 10,000-fold or more as compared with the starting material.

A "therapeutic protein" is a protein that can alleviate, reduce, prevent, delay and/or stabilize symptoms that result from an absence or defect in a protein in a cell or subject and/or is a protein that otherwise confers a benefit to a subject.

A "therapeutic RNA molecule" or "functional RNA molecule" as used herein can be an antisense nucleic acid, a ribozyme (e.g., as described in U.S. Pat. No. 5,877,022), an RNA that effects spliceosome-mediated trans-splicing (see, Puttaraju et al. (1999) *Nature Biotech.* 17:246; U.S. Pat. Nos. 6,013,487; 6,083,702), an interfering RNA (RNAi) including siRNA, shRNA or miRNA, which mediate gene silencing (see, Sharp et al., (2000) *Science* 287:2431), and any other non-translated RNA, such as a "guide" RNA (Gorman et al. (1998) *Proc. Nat. Acad. Sci. USA* 95:4929; U.S. Pat. No. 5,869,248 to Yuan et al.) and the like as are known in the art.

The terms "heterologous nucleotide sequence" and "heterologous nucleic acid molecule" are used interchangeably herein and refer to a nucleic acid sequence that is not naturally occurring in the virus. Generally, the heterologous nucleic acid comprises an open reading frame that encodes a protein or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka (1992) *Curr. Topics Microbiol. Immunol.* 158:97). Typically, the rAAV vector genome will only retain the one or more TR sequence so as to maximize the size of the trans gene that can be efficiently packaged by the vector. The structural and non-structural protein coding sequences may be provided in trans (e.g., from a vector, such as a plasmid, or by stably integrating the sequences into a packaging cell). In embodiments of the invention, the rAAV vector genome comprises at least one terminal repeat (TR) sequence (e.g., AAV TR sequence), optionally two TRs (e.g., two AAV TRs), which typically will be at the 5' and 3' ends of the vector genome and flank the heterologous nucleic acid sequence, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus (B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, or 11 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO00/28004 and Chao et al. (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 2.

TABLE 2

Naturally occurring amino acid residues.

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) and/or can be an amino acid that is modified by posttranslation modification (e.g., acetylation, amidation, formylation, hydroxylation, methylation, phosphorylation or sulfatation).

TABLE 3

Modified amino acid residues.

| Modified Amino Acid Residue Amino Acid Residue Derivatives | Abbreviation |
|---|---|
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |

TABLE 3-continued

Modified amino acid residues.

| Modified Amino Acid Residue Amino Acid Residue Derivatives | Abbreviation |
|---|---|
| Homoserine | hSer |
| Hydroxy lysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(2-F) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al. *Annu. Rev. Biophys Biomol Struct.* 35:225-49 (2006)) (the disclosure of which is incorporated herein by reference in its entirety). These unnatural amino acids can advantageously be used to chemically link molecules of interest to the AAV capsid protein.

The invention also provides a virus capsid comprising, consisting essentially of, or consisting of the virus capsid protein of the invention. In particular embodiments, the virus capsid is a parvovirus capsid, which may further be an autonomous parvovirus capsid or a dependovirus capsid. Optionally, the virus capsid is an AAV capsid. In particular embodiments, the AAV capsid is an AAV1, AAV2, AAV3a, AAV3b, AAV4, AAV5, AAV6, AAV7, AAV8, AAV9, AAV10, AAV11, or any other AAV shown in Table 1 or is derived from any of the foregoing by one or more insertions, substitutions and/or deletions.

The modified virus capsids can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules are defined as those that are not naturally found in a virus infection, e.g., those not encoded by a wild-type virus genome. Further, therapeutically useful molecules can be associated with the outside of the chimeric virus capsid for transfer of the molecules into host target cells. Such associated molecules can include DNA, RNA, small organic molecules, metals, carbohydrates, lipids and/ or polypeptides. In one embodiment of the invention the therapeutically useful molecule is covalently linked (i.e., conjugated or chemically coupled) to the capsid proteins. Methods of covalently linking molecules are known by those skilled in the art.

The invention also provides nucleic acid molecules (optionally, isolated nucleic acid molecules) encoding the virus capsids and capsid proteins of the invention. Further provided are vectors comprising the nucleic acid molecules and cells (in vivo or in culture) comprising the nucleic acid molecules and/or vectors of the invention. Suitable vectors include without limitation viral vectors (e.g., adenovirus, AAV, herpesvirus, vaccinia, poxviruses, baculoviruses, and the like), plasmids, phage, YACs, BACs, and the like. Such nucleic acid molecules, vectors and cells can be used, for example, as reagents (e.g., helper packaging constructs or packaging cells) for the production of modified virus capsids or virus vectors as described herein.

Virus capsids according to the invention can be produced using any method known in the art, e.g., by expression from a baculovirus (Brown et al. (1994) *Virology* 198:477-488).

The virus capsid proteins and virus capsids of the invention can be chimeric in that they can comprise all or a portion of a capsid subunit from another virus, e.g., as described in international patent publication WO 00/28004.

The virus capsid can be a targeted virus capsid comprising a targeting sequence (e.g., substituted or inserted in the viral capsid) that directs the virus capsid to interact with cell surface molecules present on a desired target tissue(s) (see, e.g., international patent publication WO 00/28004 and Hauck et al. (2003) *J. Virology* 77:2768-2774); Shi et al. Human Gene Therapy 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573, and 587 of the AAV2 capsid subunit]). Other positions within the AAV capsid subunit that tolerate insertions are known in the art (e.g., positions 449 and 588 described by Grifman et al. *Molecular Therapy* 3:964-975 (2001)).

For example, some of the virus capsids of the invention have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids as described by Wang et al. (*Annu. Rev. Biophys. Biomol. Struct.* 35:225-49 (2006)) can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques*, 1$^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV4, AAV5) to confer heparin binding to the resulting mutant.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, brakykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β, or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the virus capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (Current Biology 7:R318 (1997)) into the virus capsid protein. Also encompassed are peptide motifs that direct uptake by specific cells, e.g., a FVFLP peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties, polysialic acid moieties, glycoproteins, and gangliosides, MHC I glycoproteins, carbohydrate components found on membrane glycoproteins, including, mannose, N-acetyl-galactosamine, N-acetylglucosamine, fucose, galactose, and the like.

As yet a further alternative, the targeting sequence may be a peptide that can be used for chemical coupling (e.g., can comprise arginine and/or lysine residues that can be chemically coupled through their R groups) to another molecule that targets entry into a cell.

The invention also encompasses virus vectors comprising the capsid proteins and virus capsids of the invention. In particular embodiments, the virus vector can be a parvovirus vector (e.g., comprising a parvovirus capsid and/or vector genome), for example, an AAV vector (e.g., comprising an AAV capsid and/or vector genome). In representative embodiments, the virus vector comprises a virus capsid comprising a modified capsid subunit of the invention and a vector genome.

For example, in representative embodiments, the virus vector comprises: (a) a modified virus capsid (e.g., a modified AAV capsid) comprising a modified capsid protein of the invention; and (b) a nucleic acid comprising a terminal repeat sequence (e.g., an AAV TR), wherein the nucleic acid comprising the terminal repeat sequence is encapsidated by the modified virus capsid. The nucleic acid can optionally comprise two terminal repeats (e.g., two AAV TRs).

In representative embodiments, the virus vector is a recombinant virus vector comprising a heterologous nucleic acid molecule encoding a protein or functional RNA of interest. Recombinant virus vectors are described in more detail below.

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells.

Any heterologous nucleic acid sequence(s) of interest may be delivered in the virus vectors of the present invention. Nucleic acids of interest include nucleic acids encoding polypeptides, including therapeutic (e.g., for medical or veterinary uses) or immunogenic (e.g., for vaccines) proteins and/or functional or therapeutic RNA molecules.

Alternatively, in particular embodiments of this invention, the heterologous nucleic acid may encode an antisense nucleic acid, a ribozyme (e.g., as described in U.S. Pat. No. 5,877,022), RNAs that effect spliceosome-mediated trans-splicing (see, Puttaraju et al. (1999) Nature Biotech. 17:246; U.S. Pat. Nos. 6,013,487; 6,083,702), interfering RNAs (RNAi) including siRNA, shRNA or miRNA that mediate gene silencing (see, Sharp et al. (2000) Science 287:2431), and other non-translated RN As, such as "guide" RNAs (Gorman et al. (1998) Proc. Nat. Acad. Sci. USA 95:4929; U.S. Pat. No. 5,869,248 to Yuan et al.), and the like.

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid that shares homology with and recombines with a locus on a host chromosome. This approach can be utilized, for example, to correct a genetic defect in the host cell.

The present invention also provides virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al. (1994) Proc. Nat. Acad. Sci USA 91:8507; U.S. Pat. No. 5,916,563 to Young et al. U.S. Pat. No. 5,905,040 to Mazzara et al. U.S. Pat. Nos. 5,882, 652, 5,863,541 to Samulski et al.). The antigen may be presented in the parvovirus capsid. Alternatively, the antigen may be expressed from a heterologous nucleic acid introduced into a recombinant vector genome. Any immunogen of interest as described herein and/or as is known in the art can be provided by the virus vector of the present invention.

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

The virus vectors according to the present invention provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof, e.g., to express an immunogenic or therapeutic polypeptide or a functional RNA In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid encoding a polypeptide or functional RNA to treat and/or prevent any disease state for which it is beneficial to deliver a therapeutic polypeptide or functional RNA.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

In particular embodiments, the present invention provides a pharmaceutical composition comprising a virus vector and/or capsid of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

Having described the present invention, the same will be explained in greater detail in the following examples, which are included herein for illustration purposes only, and which are not intended to be limiting to the invention.

EXAMPLES

Recombinant adeno-associated viruses (AAV) are promising vectors for human gene therapy. However, current methods for evaluating AAV particle populations and vector purity are inefficient and low resolution. Here, it is shown that charge detection mass spectrometry (CDMS) can resolve capsids that contain the entire vector genome from those that contain partial genomes, and empty capsids. Measurements were performed for both single-stranded and self-complementary genomes. The self-complementary AAV vector shows a tendency to package half of the genome. Comparison with results from electron microscopy with manual particle counting shows that CDMS had no significant mass discrimination. Low abundance species can be detected by dispersing the ions in two dimensions (charge and mass). Empty AAV capsids are intrinsically heterogeneous, and capsids from different sources have slightly different masses. However, the average masses of both the empty and full capsids were in close agreement with expected values. Mass differences between the empty and full capsids for both single-stranded and self-complementary AAV vectors indicate that the genomes were packaged without counter ions. CDMS was also used to monitor the intermediates associated with thermally-activated genome release and the results show that genome release precedes capsid disintegration.

Reported herein are proof of principle studies showing that charge detection mass spectrometry (CDMS) can be used to analyze AAV vectors (packaging both single-stranded and self-complimentary genomes) as well as empty virions and potential by-products of capsid disassembly and vector genome release. The results were corroborated with EM and qPCR data. Also, the complex mass landscape of thermally-induced capsid disassembly was monitored.

AAV Vector Preparations.

All recombinant AAV vectors were generated at the UNC Vector Core facility. AAV serotype 8 (AAV8) vectors packaging an ssDNA genome with a chicken beta-actin (CBA) promoter driving a firefly luciferase transgene (Luc) or a scDNA genome with a hybrid chicken beta-actin (CBh) promoter driving a green fluorescent protein (GFP) transgene flanked by AAV2 inverted terminal repeats (ITRs) from 3-4 different production runs were individually purified using a discontinuous iodixanol gradient, followed by ion exchange chromatography. Titers were obtained by qPCR with primers for the Luc transgene. Separate fractions of purified empty and genome-containing capsids were further dialyzed into 100 mM ammonium acetate for CDMS analysis.

Charge Detection Mass Spectrometry.

Mass analysis was performed using a homebuilt charge detection mass spectrometer that has been described previously. AAV particles were ionized by nanoelectrospray and introduced into the vacuum chamber through a heated stainless-steel capillary. Ions were separated from the background gas as they passed through three differentially pumped regions containing an RF ion funnel, an RF hexapole, and an RF quadrupole, respectively. Collisional cooling in the hexapole region thermalized the ions. A DC voltage on the hexapole reaccelerated them to −100 eV per charge (z) before they entered a fourth differentially pumped region where they were focused into the entrance of a dual hemispherical deflection analyzer (HDA). The dual HDA passes a narrow band of ion kinetic energies (centered about 100 eV/z) into the fifth differentially pumped region that contained an electrostatic ion trap with a cylindrical charge detection tube. With each oscillation in the trap, the ion passed through the detector tube. The induced charge was detected by a cryogenically-cooled JFET (2SK152) and then amplified with a charge-sensitive pre-amplifier (Amptek A250). The periodic signals resulting from ion oscillation were digitized and sent to a computer for offline analysis using fast Fourier transforms. The oscillation frequency of the ions is related to the m/z and the magnitude of the fundamental is proportional to the ion charge. Charge and m/z of individual ions are multiplied to give m. Only ions that remained trapped for the entire trapping event (94 ms) are compiled and binned to create a mass histogram.

Electron Microscopy.

300-μm mesh carbon-coated copper transmission electron microscopy grids were prepared by spotting ~3 uL of AAV8 ($10^{12}$ vg/mL) on the entire grid area for ~1 minute. Grids were washed with ultrapure, HPLC-grade water and subsequently stained with 2% uranyl acetate for 1 minute. After drying, grids were imaged using a JEOL 1010 transmission electron microscope. At least 2 images for each grid were taken for qualitative analysis and up to 12 images of each grid were taken for quantitative analysis.

Results.

The AAV capsid has icosahedral symmetry (T=1) and it is assembled from 60 copies of the capsid viral protein (VP). There are three different VPs: VP1, VP2, and VP3. For AAV8, VP1 is the longest and consists of 738 residues. The VP2 sequence is identical to VP1 except that 137 residues are truncated from the N-terminus. In a similar way, the VP3 sequence is identical to VP2 except that 66 residues are truncated from the N-terminus. The number of copies of VP1, VP2, and VP3 in each capsid is thought to be stochastic with an average ratio of around 1:1:10 (i.e., there are on average five copies of VP1, five copies of VP2, and fifty copies of VP3). Masses of AAV8 VP1, VP2, and VP3 were estimated to be 81624, 66649, and 59762 Da, respectively, so the average mass of the capsid was expected to be 3.729 MDa.

FIG. 1a shows the CDMS mass spectrum measured for empty capsids separated from AAV8 vectors packaging a CBA-Luc genome. The bin width was 20 kDa. There was a large peak centered on ~3.8 MDa and a small low mass tail. CDMS is a single particle technique and, as such, the charge and mass were correlated. The points that overlay the main peak in FIG. 1a are a scatter plot of the charge and mass of each ion with masses greater than 3.4 MDa. The charge distribution for the main peak shows a single component centered on ~155 elementary charges (e).

The inset in FIG. 1a shows an expanded view of the measured peak (right peak). The left peak shows a simulation of the peak expected for a homogeneous sample of capsids consisting of only VP3 (the lightest VP) (60 copies). The width of the peak (~97 kDa FWHM) results from uncertainty in the m/z and z measurements.

The uncertainty in the charge measurement in CDMS is a function of the trapping time and oscillation frequency (and hence the m/z). Here, a trapping time of 94 ms was used, which led to a charge uncertainty of ~1.2 e for an AAV capsid with an average m/z of ~24,000 Da. For an average charge of ~155 e the relative uncertainty in the charge was ~0.8%. The relative uncertainty in the m/z measurement (0.8%) depends primarily on the ions' kinetic energy distribution. Combining the relative uncertainties from the charge and m/z leads to an overall relative uncertainty in the mass of ~1.1%. Note that this is the uncertainty associated with a single mass measurement. For many independent mass measurements the uncertainty leads to the peak width (for example, the left peak in FIG. 1 inset). The average mass (the center of the peak) can be defined more accurately than the uncertainty associated with a single mass measurement.

The center line in the inset in FIG. 1a shows the simulated peak for a stochastic mixture of VP1, VP2, and VP3 in the expected 1:1:10 ratio. To calculate this peak, the masses and abundances of all possible VP1, VP2 and VP3 compositions were first determined from a multinomial distribution. The resulting mass distribution is shown in FIG. 1b. The peaks in FIG. 1b were too close in mass to be resolved by CDMS with the conditions employed here. When accounting for the uncertainties in the m/z and z measurements, the center Gaussian peak in the inset of FIG. 1a is obtained. The peak was centered on 3.729 MDa, and was around 152 kDa wide (FWHM). It was considerably broader than the peak for the homogeneous sample (left peak) because of the distribution of VP1, VP2, and VP3 compositions that were present.

The heterogeneous mass distribution in FIG. 1b is a challenge to analyze by conventional mass spectrometry because each peak in the mass distribution leads to a number of overlapping peaks in the m/z spectrum (due to ions in different charge states). It is likely that different expression systems yield AAV particles with different compositions. For instance, some AAV capsid types with reduced levels of VP1 have been reported in first generation insect cell production systems. Newer generation systems have altered the composition of AAV capsids to include increased VP1 content, further supporting the notion that the heterogeneity of AAV capsids can be modulated.

The measured peak (the right peak in FIG. 1a) was broader than the simulated peak for the 1:1:10 ratio and shifted to a higher mass. From four independent measurements performed on different days, the average mass was 3.819±0.016 MDa (versus 3.729 MDa for the simulated peak) and the average width was 197±8 kDa (versus 152 kDa for the simulated peak). The expected and measured masses and peak widths are shown together in Table 4. The difference between the measured mass and the expected mass (2.4%) was too large to be attributed to a systematic error in the mass measurement. The shift and increased width could be due to a sample that is enriched in VP1 and VP2 or the incorporation of small DNA fragments which are known to be present during assembly.

Figure 2:
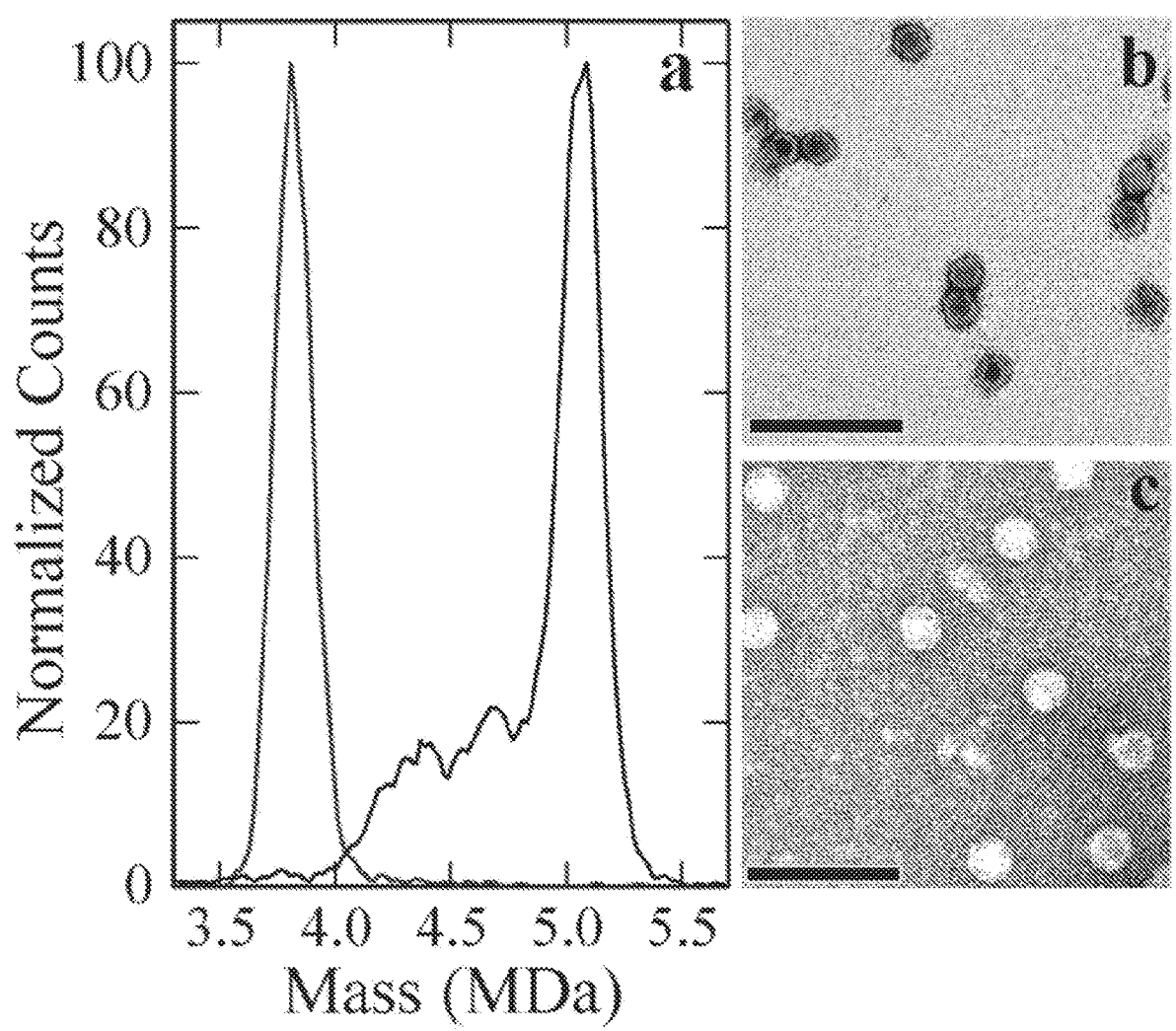
FIG. 2a is a mass histogram of separated empty (left peak) and genome-containing (right peak) AAV8 vectors packaging a ssDNA CBA-Luc cassette.
FIG. 2b is a transmission electron microscopy (TEM) image of the empty capsids of FIG. 2a, where the scale bar is 100 nm.
FIG. 2c is a TEM image of the full capsids of FIG. 2a, where the scale bar is 100 nm.

FIG. 2a shows an example of the normalized mass histogram recorded for recombinant AAV8 vectors that have packaged a single-stranded CBA-Luc genome. The histograms have been intensity normalized for comparison. The bin widths used to generate the histograms are 20 kDa. The mass histogram measured for empty particles (left peak) is overlaid. The spectrum for the genome-containing particles contained a major peak at around 5.1 MDa as well as a broad distribution extending down to roughly 4.0 MDa. The average mass of the 5.1 MDa peak was 5.080±0.013 MDa (see Table 4). The width of the peak was 208±7 kDa. The expected width was 174 kDa, so while the measured peak was slightly broader than the measured peak for the empty particles, it was actually slightly narrower when compared to the expected peak width (120% versus 130%).

The difference between the measured masses of the empty particles and the genome containing particles was 1.261±0.021 MDa. The expected mass of the CBA-Luc ssDNA genome with flanking ITRs was 1.269 MDa (see Table 4). Thus the 5.1 MDa peak is attributed to capsids that have packaged the full length vector genome. The broad distribution of ions below 5 MDa most likely highlights the presence of capsids that have packaged partial ssDNA genomes. Thus CDMS easily resolves empty and genome-containing particles. In addition, CDMS can differentiate particles that have packaged partial lengths of DNA. These results were consistent with cryo-EM analysis of AAV1 particles, which revealed that as many as four distinct capsid structures representing empty, partial and full virions can co-exist in a single AAV preparation.

The results described above were also corroborated by transmission electron micrographs of the empty capsids and recombinant AAV8 vector preparations shown in FIGS. 2b and 2c, respectively. In FIG. 2b, the donut-like structures resulted from stain entering the empty capsids, while in FIG. 2c the bright uniform structures resulted from capsids that have encapsidated the full genome while those with darkened interiors (bottom right hand corner of FIG. 2c) may be attributable to capsids with a partial genome.

The difference between the measured masses of the empty particles and the genome containing particles (1.261 MDa) was slightly less than the expected mass of the genome (1.269 MDa). The average mass of the empty particles was larger than expected. Without intending to be bound by theory, if the excess mass is partly due to the incorporation of small DNA fragments, then they would be expected to be expelled when the genome is packaged, leading to a smaller difference between the measured masses of the empty particles and the genome containing ones. The fact that the mass distribution for the full particles is slightly less heterogeneous than the empty ones was consistent with this expulsion.

The molar mass of the genome was calculated assuming that the backbone phosphates were unionized. In solution, the phosphates are expected to ionize and neutrality is retained through counter ions. The phosphate groups in the DNA backbone are known to have a strong affinity for $Na^+$. If all the $H^+$ ions associated with the backbone phosphates were replaced by $Na^+$ ions the mass of the CBA-Luc genome would increase by 90 kDa or 7.1%. The fact that the measured mass was close to the mass expected for the genome with unionized backbone phosphates suggests that the degree of incorporation of Nat or any other counter ion, was small. Although electrospray occurred from a low sodium buffer, the particles were not assembled in a low sodium environment.

Figure 3:
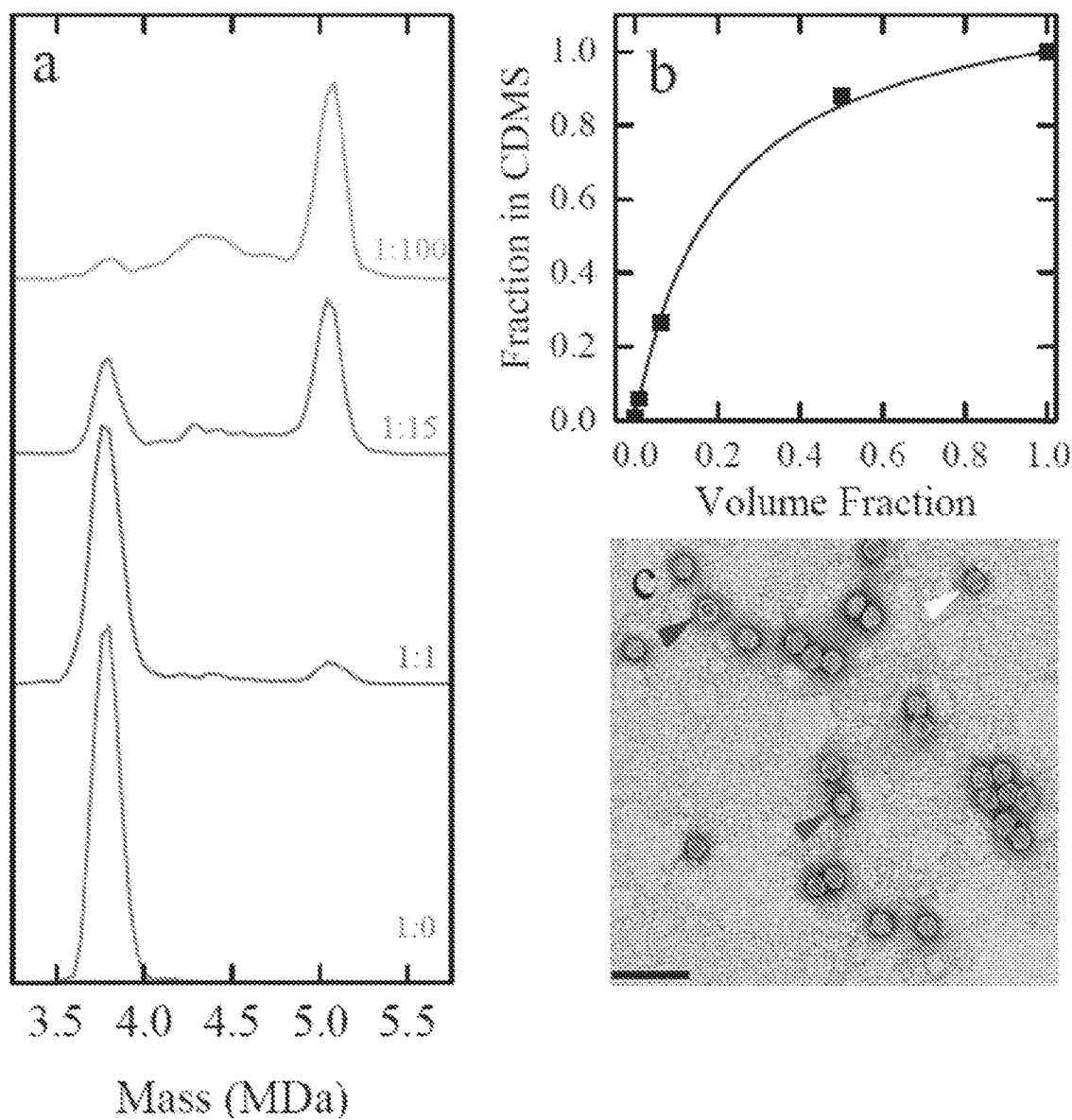
FIG. 3a is a mass histogram of empty and full capsid solutions mixed in ratios of 1:0, 1:1, 1:15, and 1:100 v:v.
FIG. 3b is a plot showing the fraction of empty particles determined from the spectra in FIG. 3a against the volume fraction of empty capsid solution used in the mixture.
FIG. 3c is a TEM image of the 1:15 v:v empty:full mixture of FIG. 3a, where the scale bar is 100 nm.

To examine how well CDMS can quantify the different types of AAV particles, stock solutions of empty and genome-containing capsids were mixed in a number of volume ratios and CDMS spectra were recorded. Typical results for empty:full ratios of 1:0, 1:1, 1:15, 1:100 are shown in FIG. 3a. FIG. 3b shows the fraction of empty particles determined from the CDMS spectra plotted against the volume fraction of empty capsid solution used in the mixture. The relationship between the fraction of empties determined by CDMS, $F_{CDMS}$, and the volume fraction, $F_V$, is:

$$F_{CDMS} = \frac{AF_V}{AF_V - F_V + 1}$$

where A is the concentration ratio of the solutions of empty and full capsids. The line in FIG. 3b is the best fit to the data using this equation. Note that if the solutions had equal concentrations, A=1 and the equation simplifies to the linear form, $F_{CDMS}=F_V$. The line is the fit to the data where A=5.84, indicating that the empty solution was 5.84 times more concentrated than the full solution.

To further examine how well CDMS can quantify the different types of AAV particles, a 1:15 mixture of the stock solutions of empty and genome-containing capsids was spotted onto EM grids for analysis by image counting. A representative portion of a transmission electron micrograph of the 1:15 mixture is shown in FIG. 3c. The image shows empty capsids (upper left arrow), full capsids (lower arrow), and partially filled capsids (upper right arrow). Because of the ambiguity in assigning capsid types, eight subjects each counted over 700 particles from 10 different images. Subjects were asked to classify the particles as empty (donut-like appearance), full (bright, uniform appearance), or ambiguous (lower contrast or differential staining pattern). As shown in Table 5, 43% of the particles analyzed by EM were deemed to contain full cargo, 30% empty capsids, and 27% ambiguous.

The assignment of a particle to a particular group depends on the incorporation of stain. To be assigned "empty," the particle must acquire enough stain to attain a donut appearance. Empty particles that acquire less stain are classified as ambiguous, or even full. Thus the number of empty particles may be underestimated. The ambiguous particles could be under-stained empty particles. On the other hand, the CDMS measurements show that there are a significant number of partially filled particles, and so the ambiguous particles could also be stained partially-filled particles. A bright uniform appearance suggests a full particle; however, this appearance could also be due to particles that are partially full (or empty) that have not picked up enough stain. Thus the number of full particles may be overestimated.

For comparison, a single CDMS histogram of the same empty/full capsid mixture used for EM analysis was fit with a series of Gaussians with widths corresponding to that of the empty peak. The areas underneath the Gaussians were used to determine the relative abundances of each particle type. Any Gaussian not associated with the empty or full capsids was assigned as ambiguous or to capsids packaging partial genomes. As shown in Table 5, 44% of the detected ions had a mass that corresponded to the capsid plus the full-length genome; 29% of ions had a mass between that of an empty and full particle; and 27% of ions had a mass corresponding to an empty capsid.

It is evident from Table 5 that the relative abundances determined by CDMS are in good agreement with those obtained from EM particle counting. The agreement is surprisingly good in view of the fact that the number of empty particles is expected to be under-counted and the number of full particles over-counted. The value in parentheses in Table 5 is the standard deviation from multiple analyses of the same data set. The standard deviations for the EM-derived data are large and reflect the high degree of subjectivity associated with classifying individual particle types. In addition to clearly differentiating between particles containing full and partial genomes, CDMS also offers the advantage of markedly reduced analysis time over EM-based counting methods. In the case of CDMS, it takes a few minutes to generate a mass histogram from the experimental data, while manual particle counting of multiple EM images to generate the data given in Table 5 took more than an hour per person.

The good agreement between the particle counting and CDMS values in Table 5 points to a lack of significant mass discrimination in the CDMS measurements. Without intending to be bound by theory, there are two main sources of discrimination associated with ion detection in CDMS. First, for ions that carry a small charge there is a possibility that the signal is lost in the noise. However, with the instrument and data analysis scheme employed here the detection efficiency is expected to be 100% for trapped ions with more than 10 charges. Thus, low detection efficiency is not expected to be an issue here, where the ions usually have more than 100 charges. The second source of discrimination is that the probability of being trapped depends on the ion velocity. Faster ions spend less time in the trap and hence they have a lower probability of being trapped. Because the ion energy is known, it is straightforward to correct for mass discrimination resulting from different ion velocities, the ions are weighed by the square root of their m/z. This correction has been included in Table 5.

Figure 4:
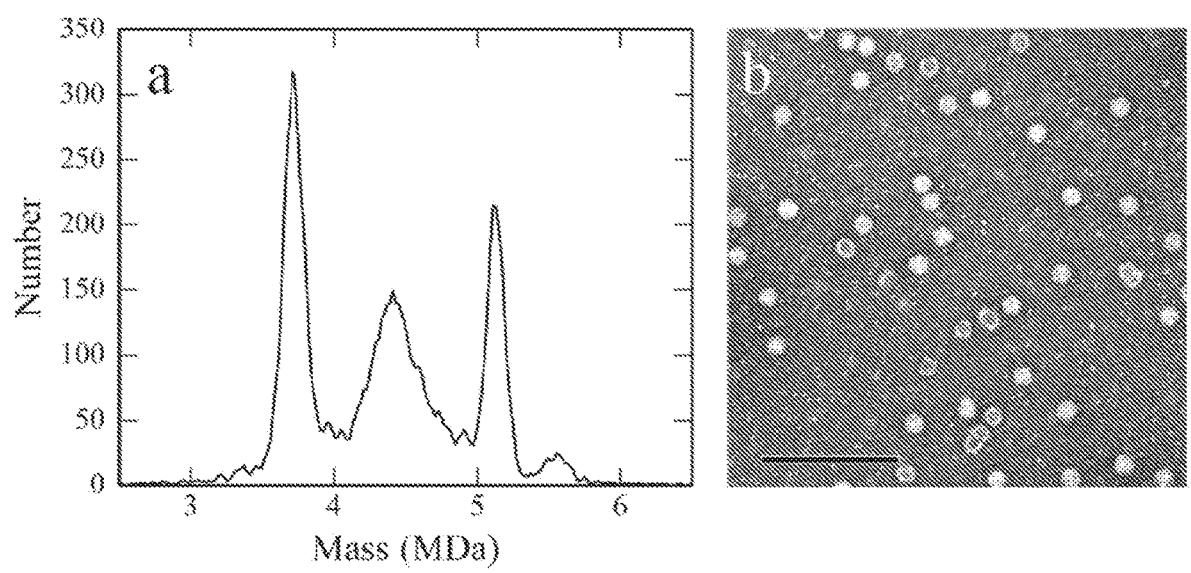

CDMS was also used to analyze AAV particles containing a self-complementary genome (scGFP, which is 4.174 kb long). FIG. 4a shows a representative CDMS mass histogram. There were four main features: two narrow, intense peaks at ~3.7 and ~5.1 MDa; a comparably intense, but broader distribution between 4 and 5 MDa; and a small peak at ~5.6 MDa. The peak at ~3.7 MDa (average mass 3.704±0.013 MDa) was close to the mass expected for the empty capsid (3.729 MDa, see Table 4). In this case the average mass was slightly less than the measured mass. The difference was small and could be due to the amount of VP1 and VP2 in this sample being slightly less than in the expected 1:1:10 ratio. The average mass of the capsid separated from the CBA-Luc-containing capsids was 3.819 MDa, so these results confirm that AAV capsids from different sources have slightly different masses.

The average mass difference between the two major peaks in FIG. 4a was 1.392±0.013 MDa. This was in good agreement with the sequence mass of the scDNA (1.389 MDa), so the peak near 5.1 MDa was assigned to the capsid with the full sc genome. A representative micrograph (FIG. 4b) is shown alongside the mass histogram. The image confirmed the presence of empty and full particles. The sequence mass for the scDNA given above was calculated for unionized DNA so the close agreement with the measured genome mass (the differences between the masses of the empty and full particles) indicates that the scDNA was packaged without counter ions. A similar conclusion was reached for the ssDNA genome discussed above.

The broad distribution between 4 and 5 MDa in FIG. 4a is attributed to partially-filled capsids. The peak in this distribution occurred roughly half-way between the peaks due to the empty and full capsids indicating a propensity to package half of the full length genome. This indicates a preference for cleaving the genome near the hairpin that joins the two self-complimentary segments. The peak attributed to packaging of a partial genome was broad indicating that there was some variability in where the genome is cleaved relative to the hairpin. In contrast, for single-stranded CBA-Luc, (FIG. 2a), the distribution of partially packaged genomes was broader and showed no tendency to package half the genome.

In FIG. 4a, approximately 35% of the capsids were empty, 23% packaged the full genome, and nearly 42% of the capsids had masses that lied between the empty and full capsids. It was found that the amount of monomeric and self-complementary genomes packaged can vary significantly for different samples with as little as 5% of the capsids containing the full genome in one case.

A scatter plot of z vs m for the scGFP-filled capsids (the mass distribution shown in FIG. 4a) is shown in FIG. 5a. Each point represents an ion. There are clusters of ions associated with empty (~3.7 MDa), partially full (4-5 MDa), and full capsids (~5.1 MDa). There are two clusters for the empty particles: the main cluster centered at ~155 e and a more-diffuse cluster centered at ~135 e. The lower-charge cluster was slightly heavier, on average, than the higher-charge cluster. Similar lower-charge clusters of ions were absent for the partially-filled and full capsids. The higher-charge cluster of empty particles, and the clusters due to the partially-full and the full capsids had similar average charges that increased slightly with mass (from ~155 to ~160 e). Finally, the small cluster of ions near 5.6 MDa had a higher average charge of ~195 e.

Figure 5:
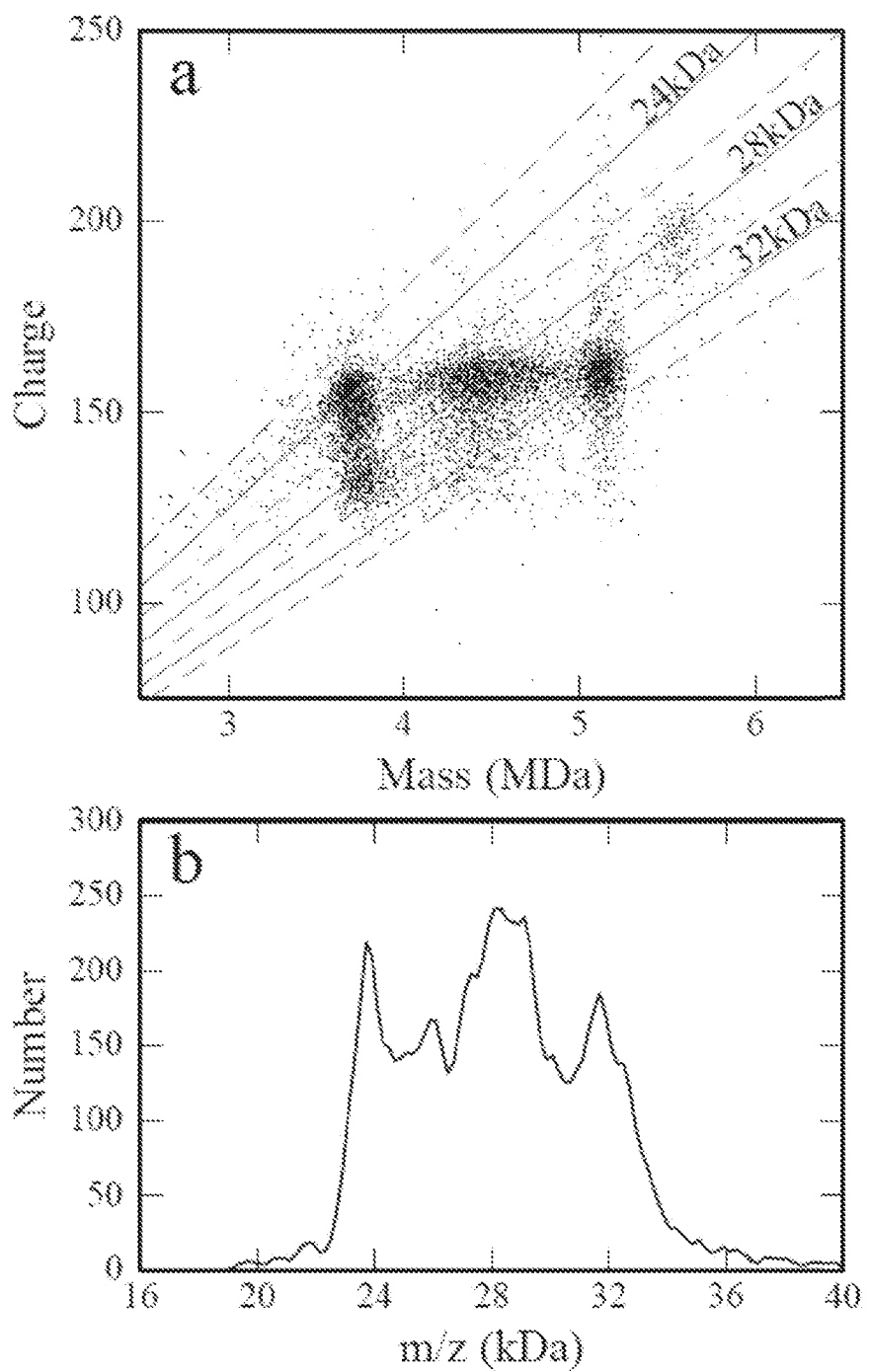

The mechanism by which ions are produced by electrospray depends on their size. The large ions studied here are expected to be generated by the charge residue mechanism. Here the water droplet containing the analyte evaporates away, leaving the ion with a charge close to the Rayleigh limit for a water droplet with the same radius as the analyte. Inspection of FIG. 5 shows that the main clusters of ions associated with the empty, partial and full capsids had similar charges indicating that the genome and partial genome are packaged inside the capsid. If some of the genome extended outside the capsid the charges would be higher. Indeed this may explain the tail of highly charged ions that extend from the cluster due to the full particles (see FIG. 5a).

There were two distinct charge state distributions for the empty capsids in FIG. 5. The absence of low charge clusters for the partial and full capsids in FIG. 5 can be attributed to the presence of the genome, which presumably helps the capsids resist compaction. Even a partial genome may be enough to prevent compaction. A low charge cluster of ions was also not observed in the charge versus mass scatter plot for the empty particles separated from AAV8 vectors packaging a CBA-Luc genome (FIG. 1). The scatter plot for these ions shows a single cluster centered at ~155 e. However, the masses of the separated AAV8 particles were significantly larger than expected for empty particles (see Table 4), leading to the suggestion that they may have contained small DNA fragments.

The small peak at ~5.55 MDa in FIG. 4a was probably due to an impurity. If it was attached to the full capsid then its mass was around 416±25 kDa. The fact that the ions in this peak had significantly higher average charge than the full particles (see FIG. 5) suggests that the impurity was outside the capsid where it increased the average radius of the ion. Note that there is no evidence for the same impurity attached to the outside of the empty capsid. Such a low abundance impurity attached to the empty capsid would be difficult to detect in the mass distribution shown in FIG. 4a, however, it would be easy to detect in the charge versus mass scatter plot.

Since the average charges on the empty, partial, and full particles are similar it is possible that useful information on their relative abundances could be obtained from the m/z distribution that is accessible from conventional mass spectrometry methods, even without charge state resolution. The diagonal lines in the charge versus mass plot (FIG. 5a) show lines of constant m/z. The m/z histogram is shown in FIG. 5b. There are peaks 24, 28, and 32 kDa. Inspection of FIG. 5a shows that these are due to empty, partial, and full capsids. As such, the m/z spectrum alone can reveal some information about the composition. However, the components were more poorly resolved and their relative abundances were different from in the mass distribution. Inspection of FIG. 5a reveals the origin of the difference. The low charge component of the empty capsids has m/z values (~28 kDa) similar to the partially filled particles, as does the high mass component at ~5.55 MDa. Thus the m/z distribution underestimates the empty capsids, overestimates the partial, and cannot detect the high mass impurity.

Figure 6:
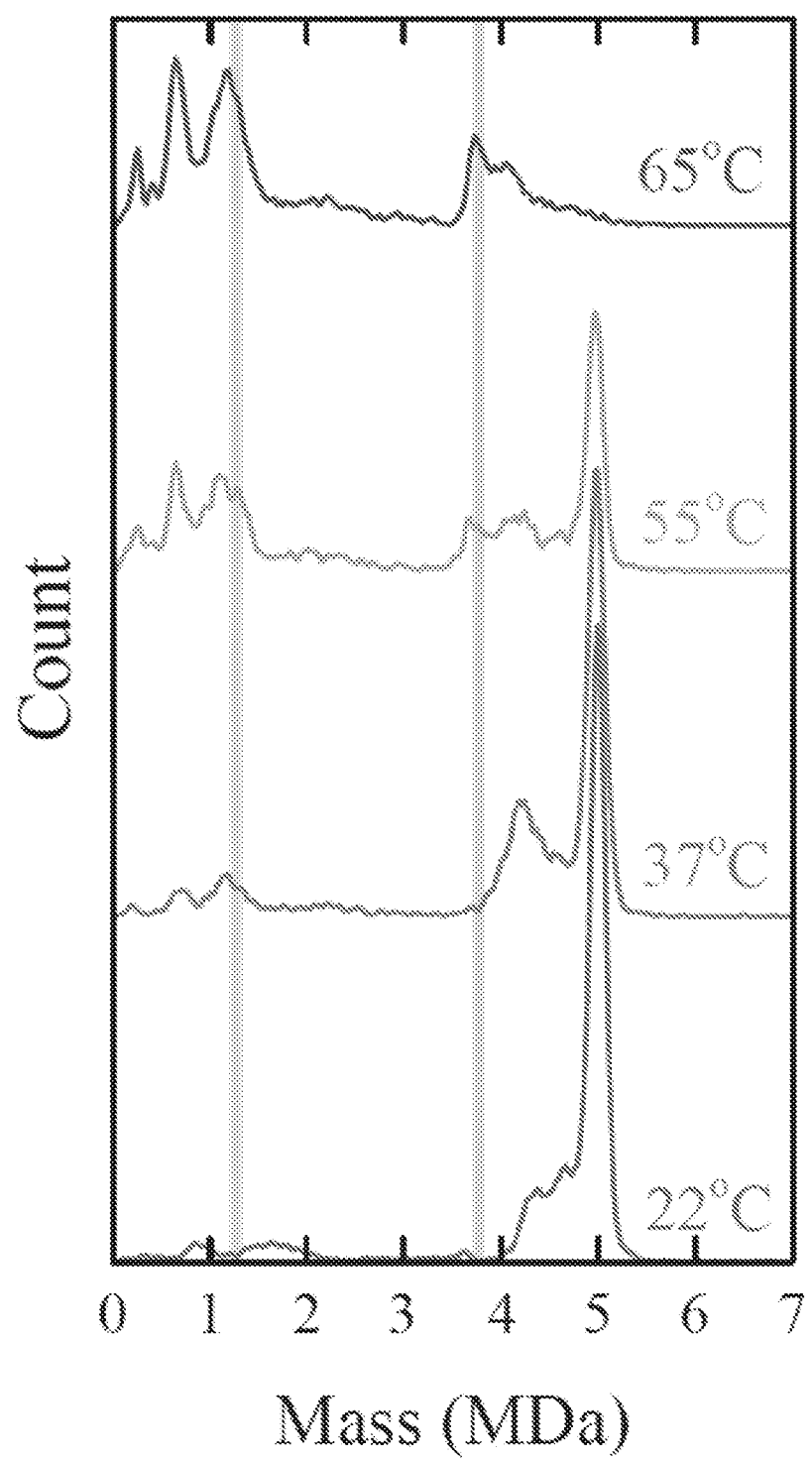
FIG. 6 is a mass histogram for thermal-induced uncoating of purified AAV8 capsids packaging a ssDNA CBA-Luc genome.

In addition to AAV particle diversity, potential contaminants of clinical AAV preparations included molecular contaminants from producer cell lines, the media, AAV capsid fragments, VP subunits and/or free vector genomic DNA. To map the mass landscape associated with AAV particle disassembly, capsids were heated to 37° C., 55° C., and 65° C. for 30 minutes and immediately chilled to 4° C. prior to mass analysis. The CDMS histograms of the thermal scan are shown in FIG. 6, wherein each individual spectrum has been normalized to the same total number of ions and the bin widths used to generate the histograms are 40 kDa. The bottom spectrum (22° C.) corresponds to intact AAV8 capsid packaging a full length CBA-Luc genome as established earlier. Upon heating to 37° C., the mass distribution reveals that a large portion of the capsid/genome complex remained largely intact, although modest increases in intensity at 4.2 MDa as well as lower mass species at 0.65 and 1.2 MDa were observed. A decrease in intensities for both full and partial capsid mass signals was observed. Heating to 55° C. resulted in an increase in the relative intensity of the low mass ions, including peaks corresponding to the masses of the empty capsid and the free, full length genome (3.729 MDa and 1.269 MDa, respectively) as indicated by the vertical bars marking the corresponding masses. The intensity of the full capsid peak decreased to 40% of the initial intensity under these conditions. Lastly, heating to 65° C. resulted in the complete disassembly of partial and full length genome-containing particles, an increase in peak intensities at ~1.3 MDa and ~3.7 MDa, corresponding to the empty particle and free, full length genome as indicated earlier. Although not resolvable separately, the lower masses can likely be attributed to capsid fragments and/or partial ssDNA vector genomes. Thus, in addition to quantitative assessment of AAV particle purity, CDMS can monitor the complex mass landscape resulting from capsid disassembly during storage and arguably during the infectious pathway and within the nucleus following genome release. These results also corroborate earlier observations through EM, AFM and biophysical analysis that AAV capsids disassemble and eject their genomes in response to increasing thermal stress.

Figure 7:
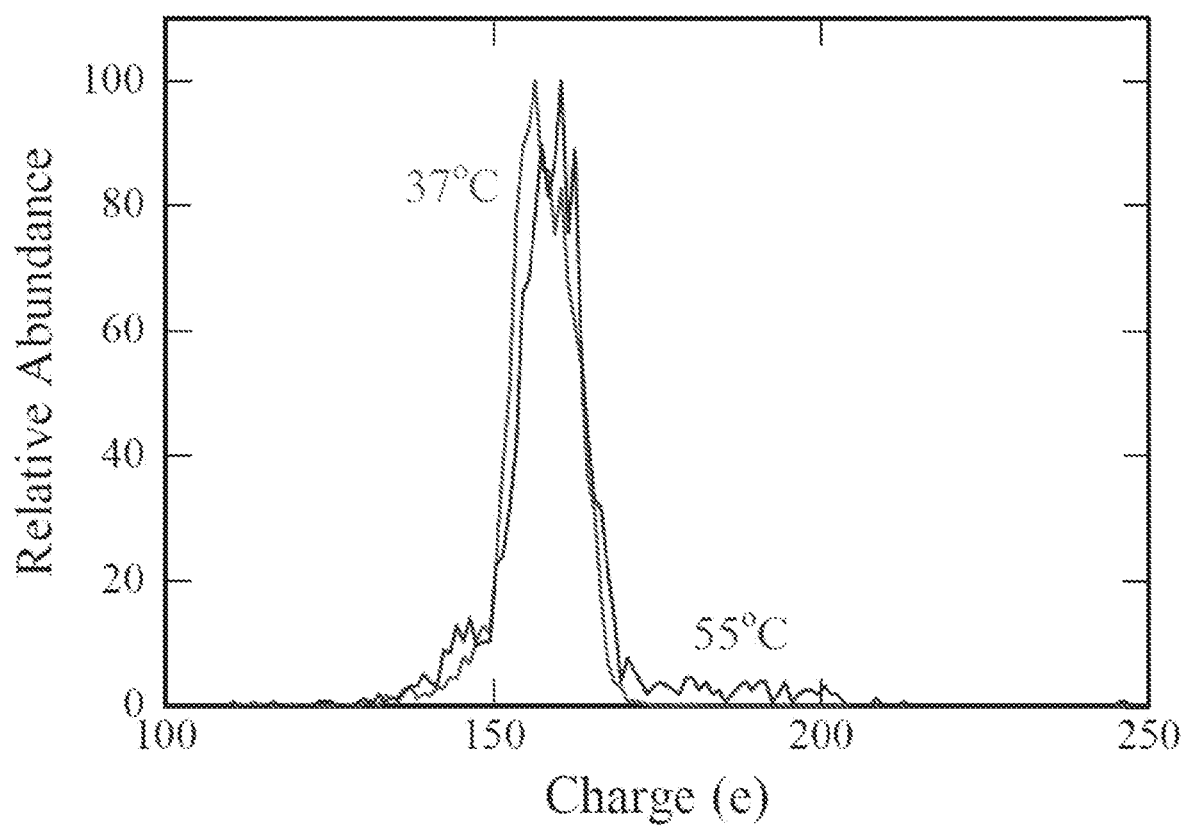
FIG. 7 is a charge distribution for the mass peak corresponding to the full capsid in FIG. 6 (~5.0 MDa).

The charge distributions may provide some insight into how the genome is expelled. Charge distributions for the peak in the mass distribution for the particle with the full length genome (the peak at ~5.0 MDa in FIG. 6) are shown in FIG. 7 for temperatures of 37° C. (left peak) and 55° C. (right peak). The results at 22° C. are almost identical to those at 37° C., which show a single Gaussian-shaped peak centered at ~160 e. At 55° C., the size of the peak in the mass distribution due to the full particle was considerably diminished (see FIG. 6) and a small high charge tail had emerged in the charge distribution. This high charge tail could be due to particles caught in the act of expelling the genome. Support for this interpretation comes from the fact that there is not a corresponding tail in the charge distribution for the empty particle. At 65° C. the peak due to the full particle had disappeared.

TABLE 4

Compilation of expected and measured masses and FWHM peak widths. Empty AAV8 capsids were measured after separation from CBA-Luc-containing capsids and from a sample which packaged scGFP. The measurements for these two samples of empty capsids are grouped together with the appropriate genome.

|  | Expected Mass (MDa) | Measured Mass (MDa) | Difference (kDa) | Expected FWHM (kDa) | Measured FWHM (kDa) |
|---|---|---|---|---|---|
| 60 copies AAV8 VP3 | 3.586 |  |  | 97 |  |
| AAV8 Capsid | 3.729 | 3.819 ± 16 | +90 | 152 | 195 ± 8 |

TABLE 4-continued

Compilation of expected and measured masses and FWHM peak widths. Empty AAV8 capsids were measured after separation from CBA-Luc-containing capsids and from a sample which packaged scGFP. The measurements for these two samples of empty capsids are grouped together with the appropriate genome.

|  | Expected Mass (MDa) | Measured Mass (MDa) | Difference (kDa) | Expected FWHM (kDa) | Measured FWHM (kDa) |
|---|---|---|---|---|---|
| CBA-Luc genome | 1.269 | 1.261 ± 21 | −8 | | |
| AAV8/CBA-Luc | 4.998 | 5.080 ± 13 | +82 | 174 | 208 ± 7 |
| AAV8 Capsid | 3.729 | 3.704 ± 13 | −25 | 152 | 180 ± 5 / 155 ± 11 |
| scGFP Genome | 1.389 | 1.392 ± 13 | +3 | | |
| AAV8/ scGFP | 5.118 | 5.095 ± 25 | −23 | 177 | 172 ± 15 | a) See text for masses of VP1, VP2, and VP3.
b) For a stochastic mixture of VP1, VP2, and VP3 in an average ratio of 1:1:10.
c) Sequence mass calculated using http://www.bioinformatics.org/sms2/dna_mw.html
d) For the higher charge cluster of empty capsids in FIG. 5.

TABLE 5

Comparison of the AAV particle types determined by electron microscopy with manual image counting (EM) and charge detection mass spectrometry (CDMS). The numbers indicate the fractions of the different particle types in the 1:15 v:v mixed sample. Numbers in parentheses are standard deviations for multiple analyses of the same data set.

|  | Full | Ambiguous/Partial | Empty |
|---|---|---|---|
| EM | 0.43 (±0.16) | 0.27 (±0.15) | 0.30 (±0.16) |
| CDMS | 0.421 (±0.004) | 0.288 (±0.006) | 0.291 (±0.002) |

In conclusion, CDMS can rapidly establish the purity of AAV vector preparations by resolving the particles into empty, partial and full sub-populations. The sc AAV vector shows a tendency to package half of the genome. The close agreement between CDMS results and electron microscopy with manual particle counting confirms expectations that mass discrimination is small in the relevant mass range. The single particle resolution of AAV vector preparations by CDMS allows for rapid screening and quality testing of clinical samples. Because the empty, partial and full capsids have similar charges (as expected from the charge residue model) it is possible to obtain some abundance information from the m/z spectra alone, even without charge state resolution. However, CDMS provides much more reliable information and low abundance species can be detected by dispersing the ions in two dimensions (charge and mass). The differences between the masses of the empty and full particles, for both the ss and sc genomes, indicate that in both cases the DNA is packaged without counter ions. CDMS can map the entire mass landscape associated with thermally-induced genome ejection and capsid disassembly.

The invention claimed is:

1. A method of identifying components present in a preparation of virus particles, the method comprising:
   a) ionizing virus particles in the preparation of virus particles;
   b) subjecting the ionized virus particles to single-particle mass spectrometry to determine a mass of each of the ionized virus particles; and
   c) identifying the components based on the determined masses of the ionized virus particles;
   wherein the identified components comprise an impurity present in the preparation or each of full genome-containing virus particles, partial genome-containing virus particles and genome-free virus particles.

2. The method of claim 1, wherein the single-particle mass spectrometry comprises charge detection mass spectrometry.

3. The method of claim 1, wherein the genome comprises a single-stranded genome or a self-complementary genome.

4. The method of claim 1, further comprising heating the virus particle;
   wherein identifying the components further comprises monitoring thermally-induced capsid disassembly of at least one of the full genome-containing virus particles, the partial genome-containing virus particles and the genome-free virus particles.

5. The method of claim 4, wherein the virus particles are heated to at least 35° C.

6. The method of claim 4, wherein the virus particles are heated to at least 50° C.

7. The method of claim 1, further comprising producing a mass histogram of the ionized virus particles subjected to the single-particle mass spectrometry and identifying the components based on the mass histogram.

8. The method of claim 1, wherein the virus particles are selected from the group consisting of adeno-associated virus (AAV), adenovirus, lentivirus, retrovirus, herpesvirus, poxvirus (vaccinia or myxoma), paramyxovirus (measles, RSV or Newcastle disease virus), baculovirus, reovirus, alphavirus, flavivirus, and any combinations thereof.

9. The method of claim 1, wherein one or more of the virus particles are complexed with an exogenous entity.

10. The method of claim 9, wherein the exogenous entity is selected from the group consisting of a protein, a nucleic acid, a carbohydrate molecule, and combinations thereof.

11. The method of claim 1, further comprising distinguishing the components based on differences in the determined masses of the ionized virus particles.

12. The method of claim 1, wherein the identified components comprise the impurity present in the preparation;
   and wherein the method further comprises detecting the impurity based on differences in the determined masses of the ionized virus particles.

13. The method of claim 1, wherein the method does not comprise electron microscopy.

14. The method of claim 1, wherein the components present in the preparation of virus particles are selected from the group consisting of full genome-containing virus particles, partial genome-containing virus particles, genome-free virus particles, empty virus capsids and fragments thereof, genomic components and fragments thereof, packaged genomes and fragments thereof, unpackaged nucleic acid, contaminants, and any combination thereof.

15. The method of claim 1, wherein the single particle mass spectrometry is performed by time of flight mass spectrometry, charge detection mass spectrometry, quadrupole ion trap mass spectrometry, Fourier transform ion cyclotron resonance, Orbitrap mass spectrometry or carried out using a micromechanical/nanomechanical oscillator.

16. The method claim 1, wherein the single particle mass spectrometry is carried out on a commercial mass spectrometer retro-fitted for single particle measurements.

17. The method of claim 1, wherein the preparation of virus particles is a research grade preparation.

18. The method of claim 1, wherein the preparation of virus particles is a GMP grade preparation.

19. The method of claim 1, wherein the preparation of virus particles is a commercial preparation.

20. The method of claim 1, wherein the method is carried out in about 20 minutes.

* * * * *